United States Patent
Shameli et al.

(10) Patent No.: US 12,220,162 B2
(45) Date of Patent: Feb. 11, 2025

(54) TURBINATE REDUCTION INSTRUMENT

(71) Applicant: Acclarent, Inc., Irvine, CA (US)

(72) Inventors: Ehsan Shameli, Irvine, CA (US); Jetmir Palushi, Irvine, CA (US); Itzhak Fang, Irvine, CA (US); Athanasios Papadakis, Newport Beach, CA (US); William J. Kane, Newport Coast, CA (US); Fatemeh Akbarian, Rancho Palos Verdes, CA (US)

(73) Assignee: Acclarent, Inc., Irvine, CA (US)

( * ) Notice: Subject to any disclaimer, the term of this patent is extended or adjusted under 35 U.S.C. 154(b) by 782 days.

(21) Appl. No.: 17/096,346

(22) Filed: Nov. 12, 2020

(65) Prior Publication Data

US 2021/0161589 A1 Jun. 3, 2021

Related U.S. Application Data

(60) Provisional application No. 62/942,786, filed on Dec. 3, 2019.

(51) Int. Cl.
*A61B 18/14* (2006.01)
*A61B 90/00* (2016.01)
*A61B 18/00* (2006.01)

(52) U.S. Cl.
CPC .......... *A61B 18/1485* (2013.01); *A61B 90/39* (2016.02); *A61B 2018/00208* (2013.01); *A61B 2018/00327* (2013.01); *A61B 2018/00607* (2013.01); *A61B 2018/1412* (2013.01); *A61B 2090/3937* (2016.02)

(58) Field of Classification Search
CPC ..... A61B 5/287; A61B 5/6858; A61B 5/6859; A61B 5/6869; A61B 18/1492; A61B 2018/0016; A61B 2018/00267; A61B 2018/00351; A61B 2018/00357; A61B 2018/00577; A61B 2018/00839; A61B 2217/007; A61B 2218/002; A61B 2562/221; A61N 1/362
See application file for complete search history.

(56) References Cited

U.S. PATENT DOCUMENTS

| | | | |
|---|---|---|---|
| 5,718,702 A * | 2/1998 | Edwards | ................ A61B 18/18 606/41 |
| 7,720,521 B2 | 5/2010 | Chang et al. | |
| 8,461,744 B2 | 6/2013 | Wiener et al. | |
| 8,465,491 B2 | 6/2013 | Yedlicka et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 9,095,367 B2 | 8/2015 | Olson et al. | |

(Continued)

*Primary Examiner* — Eun Hwa Kim
*Assistant Examiner* — Catherine Premraj
(74) *Attorney, Agent, or Firm* — Morgan, Lewis & Bockius LLP

(57) ABSTRACT

A surgical instrument includes a handle assembly and a shaft assembly extending distally from the handle assembly and having a distal end sized to be inserted into the nasal cavity of a patient. The shaft assembly includes a cutting member configured to cut tissue within the nasal cavity, and a translating member slidably disposed over the cutting member. A navigation sensor is disposed within the distal end of the shaft assembly and is operable to generate a signal corresponding to a position of the distal end within the patient.

14 Claims, 28 Drawing Sheets

(56) References Cited

U.S. PATENT DOCUMENTS

| | | |
|---|---|---|
| 9,572,622 B2 | 2/2017 | Shelton, IV et al. |
| 9,750,521 B2 | 9/2017 | Lamping et al. |
| 9,913,709 B2 | 3/2018 | Housman et al. |
| 9,949,785 B2 | 4/2018 | Price et al. |
| 10,463,242 B2 | 11/2019 | Kesten et al. |
| 10,524,869 B2 | 1/2020 | Jenkins et al. |
| 10,561,370 B2 | 2/2020 | Salazar et al. |
| 2003/0135223 A1* | 7/2003 | Teague ................ A61B 17/221 606/127 |
| 2011/0258843 A1* | 10/2011 | Dukesherer ............. A61B 5/06 29/606 |
| 2014/0277039 A1* | 9/2014 | Liberatore ....... A61B 17/32053 606/167 |
| 2014/0364725 A1 | 12/2014 | Makower |
| 2015/0081017 A1 | 3/2015 | Abbate et al. |
| 2016/0022283 A1 | 1/2016 | Wallace et al. |
| 2016/0324531 A1 | 11/2016 | Gross et al. |
| 2017/0000541 A1 | 1/2017 | Yates et al. |
| 2019/0099195 A1 | 4/2019 | Carroll et al. |

\* cited by examiner

TURBINATE REDUCTION INSTRUMENT

PRIORITY

This application claims priority to U.S. Provisional Pat. App. No. 62/942,786, entitled "Turbinate Reduction Instrument," filed Dec. 3, 2019, the disclosure of which is incorporated by reference herein, in its entirety.

BACKGROUND

FIG. 1 shows a left sagittal cross-sectional view of a portion of a human head, which includes a nasal cavity (NC), a lateral nasal wall (LNW), a sphenoid sinus (SS), an ethmoid sinus (ES), a frontal sinus (FS), middle turbinate horizontal basal lamella (MThBL), middle turbinate vertical basal lamella (MTvBL), and an uncinate process (UP). The ethmoid sinus (ES) comprises a set of sinus cells that may be categorized as anterior ethmoid sinus (AES) cells and posterior ethmoid sinus (PES) cells. The ethmoid bulla (EB) is the largest ethmoid sinus (ES) cell and is generally inferior and anterior to the other cells of the ethmoid sinus (ES). The posterior wall of the ethmoid bulla (EB) and the middle turbinate vertical basal lamella (MTvBL) together define a retrobullar space (RBS). It should be understood that anatomical variation in the human is such that this retrobullar space (RBS) may or may not be present in a given individual.

The ethmoid sinus (ES) includes ostia (not shown) for providing fluid communication to and from the cells of the ethmoid sinus (ES) and the nasal cavity. For instance, ostia may provide fluid paths for cells within the anterior ethmoid sinus (AES), cells within the posterior ethmoid sinus (PES), and the ethmoid bulla (EB). In some instances, suprabullar cells of the ethmoid sinus (ES) drain into the ethmoid bulla (EB). Some suprabullar cells may drain directly into the retrobullar space (RBS). The ethmoid bulla (EB) may itself provide fluid communication with the nasal cavity via one or more ostia, such that the ethmoid bulla (EB) may provide a fluid communication path between the other ethmoid sinus (ES) cells (that drain into the ethmoid bulla (EB)) and the nasal cavity. For instance, the ethmoid bulla (EB) may provide fluid communication through an ostium at the retrobullar space (RBS). The fluid communication paths provided by ostia may allow the entry of air and liquids (e.g., medications); while also allowing drainage of mucus. In some instances, the ostia may become blocked, may become functionally closed due to mucosal thickening, or may otherwise not provide sufficient fluid communication. In addition, or in the alternative, the configuration of the retrobullar space (RBS) may impede flow through the ostium of the ethmoid bulla (EB).

In some instances, it may be desirable to perform remodeling surgery on an anatomical structure accessible from within the nasal cavity (NC) of a patient, for example to reshape a portion of the structure to promote improved fluid drainage and/or airflow. By way of example only, such remodeling surgeries may be performed on a sinus wall for improved drainage from and ventilation of the sinus, or on a nasal turbinate (LT, MT, UT) for improved airflow through the nasal cavity (NC). Exemplary instruments operable for performing such remodeling procedures are described in U.S. Pat. No. 10,524,869, entitled "Apparatus and method for Treatment of Ethmoid Sinusitis," issued Jan. 7, 2020, the disclosure of which is incorporated by reference herein.

In some instances, it may be desirable to track the position of an instrument within a patient during a surgical procedure. Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While several systems and methods have been made and used in ENT procedures, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
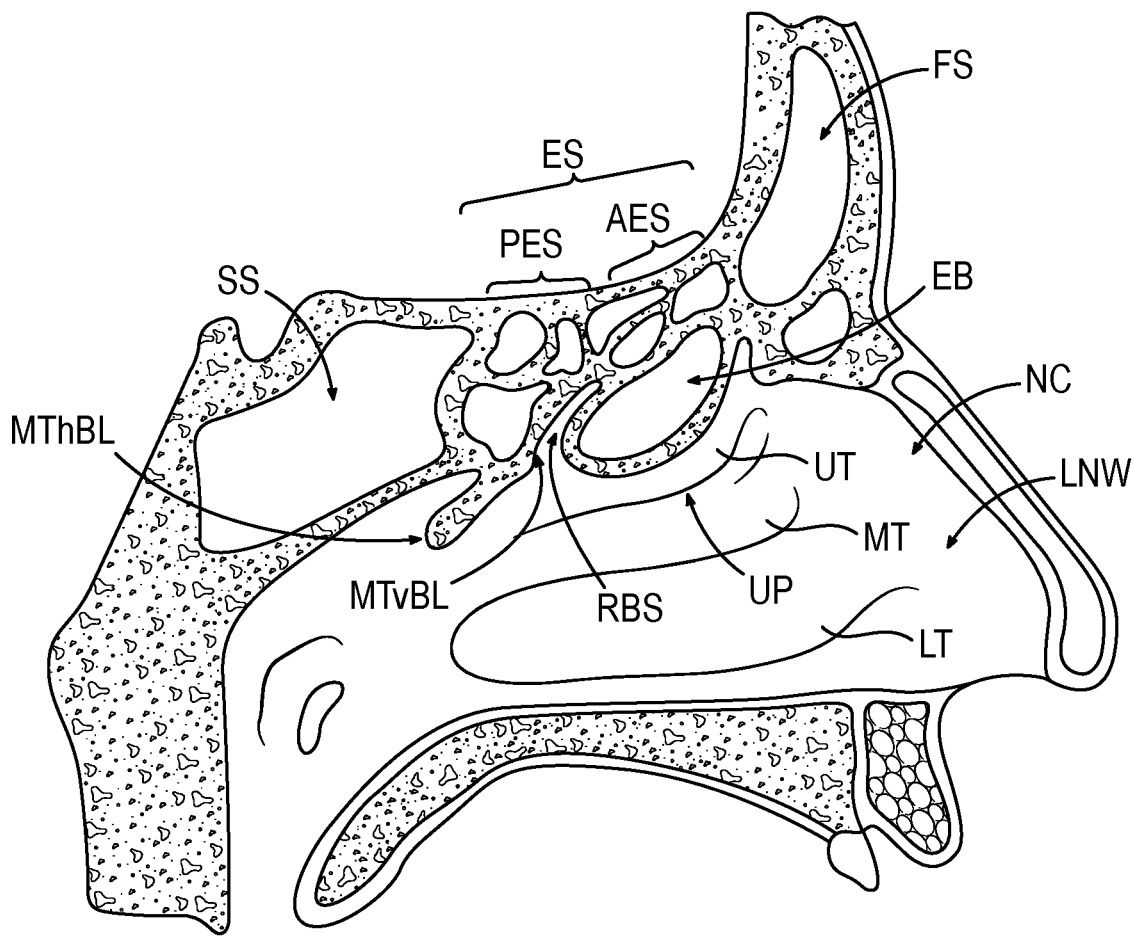
FIG. 1 depicts a left sagittal cross-sectional view of a portion of a human head, showing paranasal sinus structures.
Figure 2:
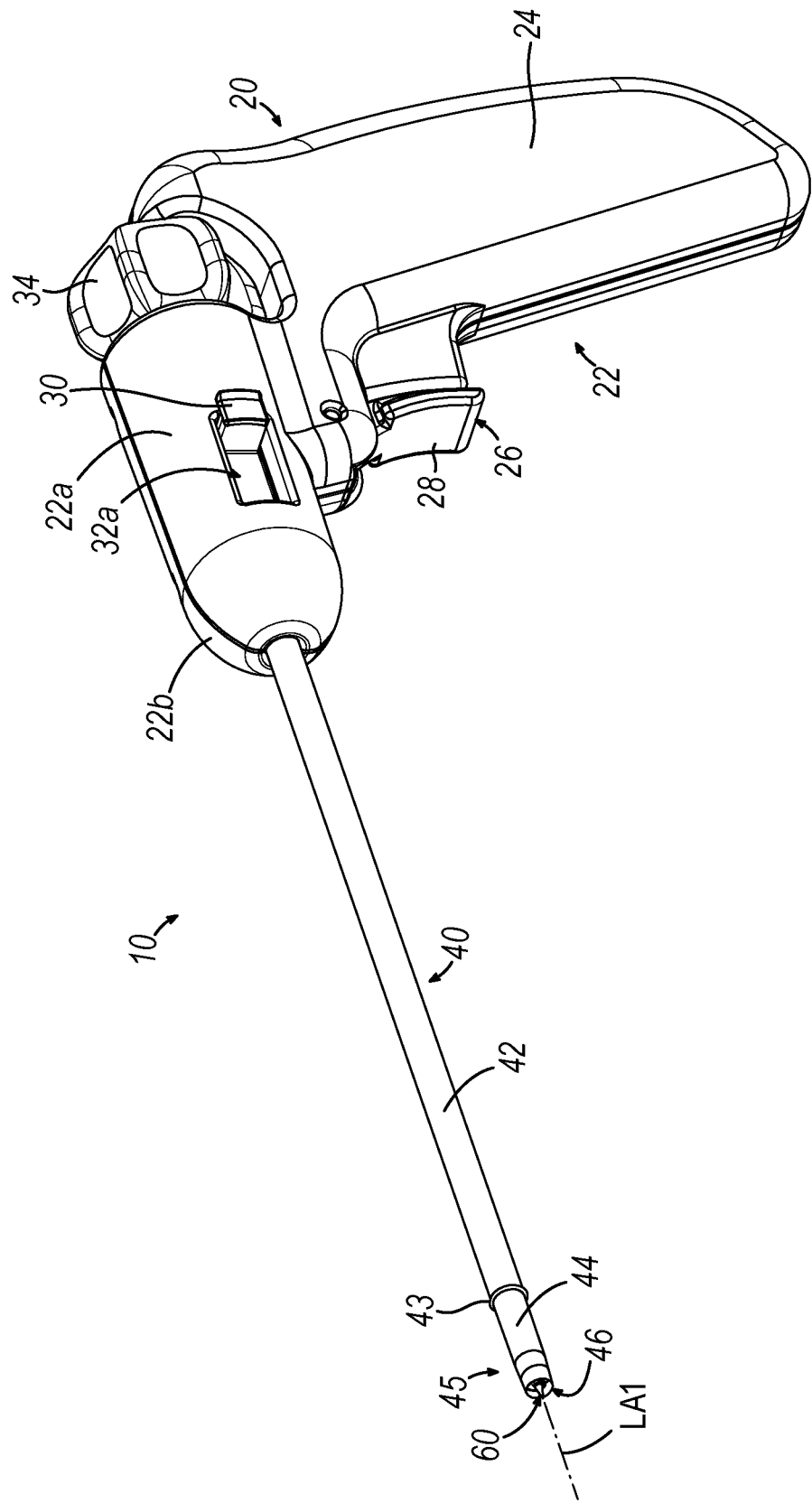
FIG. 2 depicts a perspective view of an exemplary surgical piercing instrument for piercing a wall within the nasal cavity.
Figure 3:
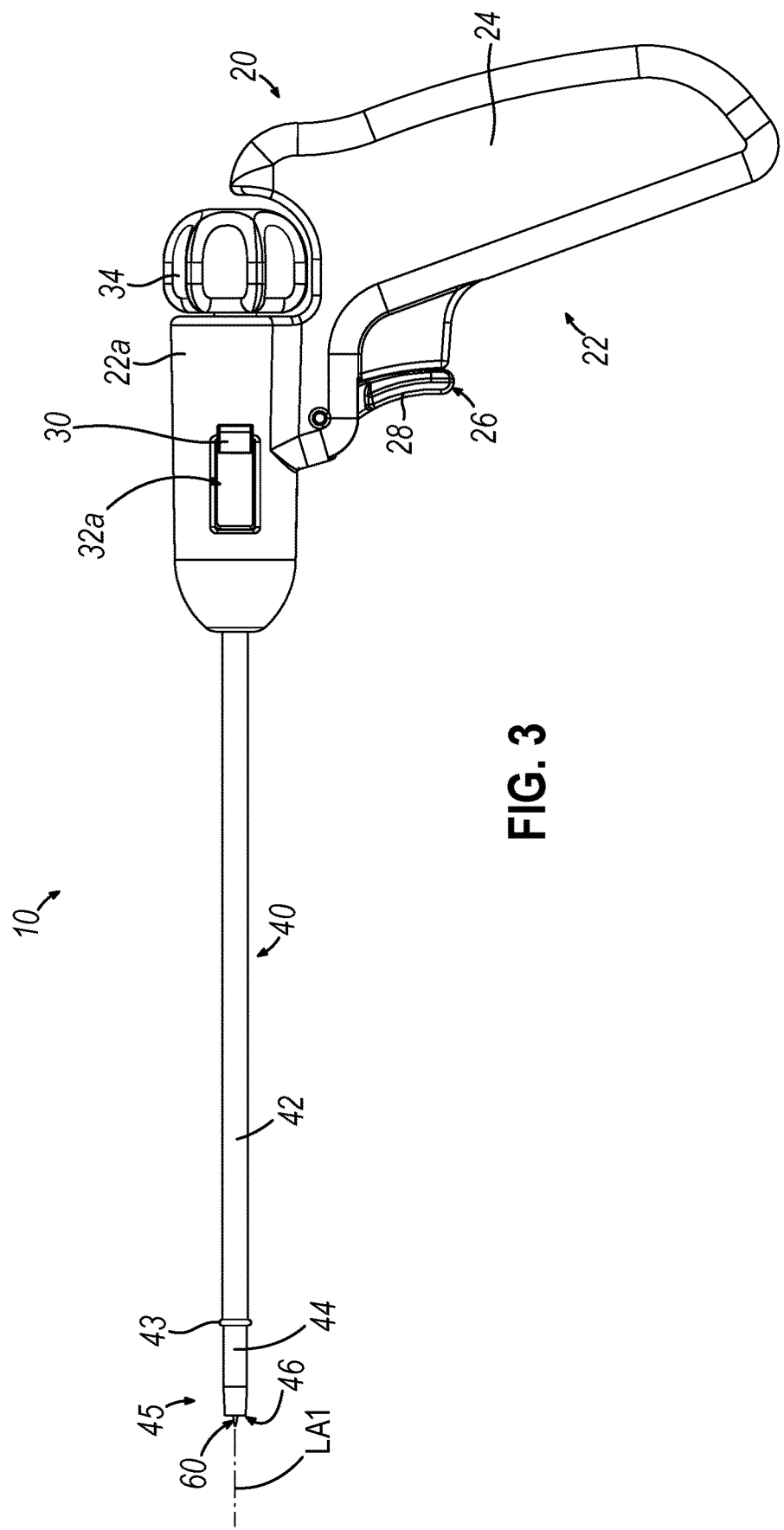
FIG. 3 depicts a side elevational view of the instrument of FIG. 2.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Exemplary Piercing Instrument with Helical Auger and Retractable Sheath

The wall defining a sinus cavity may be pierced for various purposes, including but not limited to deploying a port, deploying a wick, or simply creating a new ostium. Several examples of instruments that may be used to pierce the wall of a sinus cavity are described in U.S. Pat. No. 10,524,869, incorporated by reference above. It should be understood that sinus wall piercing elements may include trocar type tips, coring tips, and other types of tips. Such tips may be advanced without rotation, advanced with rotation (e.g., in full rotations or angularly reciprocating partial rotations), advanced with longitudinal reciprocation (e.g., in a jackhammering action), or advanced with both rotation and longitudinal reciprocation. Piercing tips may have a sharp edge and/or an abrasive edge. As used herein, the term "piercing" should be understood to include various forms of cutting. For instance, a piercing element may also be configured to cut a slice out of a sinus wall. This may include corner slicing, medial slicing, or other forms of slicing/cutting. In some instances, an act of cutting leaves a mucosal flap that can cover over exposed bone. When a cut leaves exposed bone or a tattered tissue edge, the same may be covered with a conformal material and/or curing material. An exemplary version of a piercing/cutting element will be described in greater detail below; while further examples will be apparent to those of ordinary skill in the art in view of the teachings herein.

A. Overview of Exemplary Piercing Instrument

FIGS. 2-5 show an exemplary piercing instrument (10) that may be used to form an opening in a wall within the nasal cavity, such as a sinus wall (SW) as shown in FIGS. 10A-11F described below. By way of example only, the sinus wall (SW) may be a wall of the ethmoid bulla (EB) (e.g., the anterior face of the ethmoid bulla (EB)) or the wall of some other sinus cavity. Instrument (10) of the present example comprises a handle assembly (20) and a shaft assembly (40). Handle assembly (20) comprises a first body portion (22A) and a second body portion (22B) coupled together to form a body (22). Body (22) defines a pistol grip (24) in the present example, though it should be understood that body (22) may alternatively provide a variety of alternative grip configurations.

Handle assembly (20) further includes a pivoting trigger (26) that is pivotable toward and away from pistol grip (24). As shown in FIGS. 32-35, pivoting trigger (26) includes a paddle (28) extending downwardly from body (22) such that a user may actuate pivoting trigger (26) with a finger or thumb of a hand that is grasping pistol grip (24). As will be discussed in more detail below, actuation of pivoting trigger (26) causes longitudinal movement of a cutter tube (44) of shaft assembly (40). Handle assembly (20) also includes a sliding trigger (30) that is longitudinally slidable between a proximal position and a distal position within an internal channel (50) of body (22). Portions of sliding trigger (30) project laterally from a pair of slots (32A, 32B) formed respectively in first body portion (22A) and second body portion (22B) such that a user may actuate sliding trigger (30) with a finger or thumb of a hand that is grasping pistol grip (24). As will be discussed in more detail below, actuation of sliding trigger (30) causes longitudinal movement of an outer sheath (42) of shaft assembly (40). Handle assembly (20) further includes a rotatable knob (34) that is rotatable about a longitudinal axis (LA1) defined by shaft assembly (40). As will be discussed in more detail below, actuation of rotatable knob (34) cause rotation of a rotatable shaft (46) of shaft assembly (40) relative to handle assembly (20) and relative to other components of shaft assembly (40).

Figure 5:
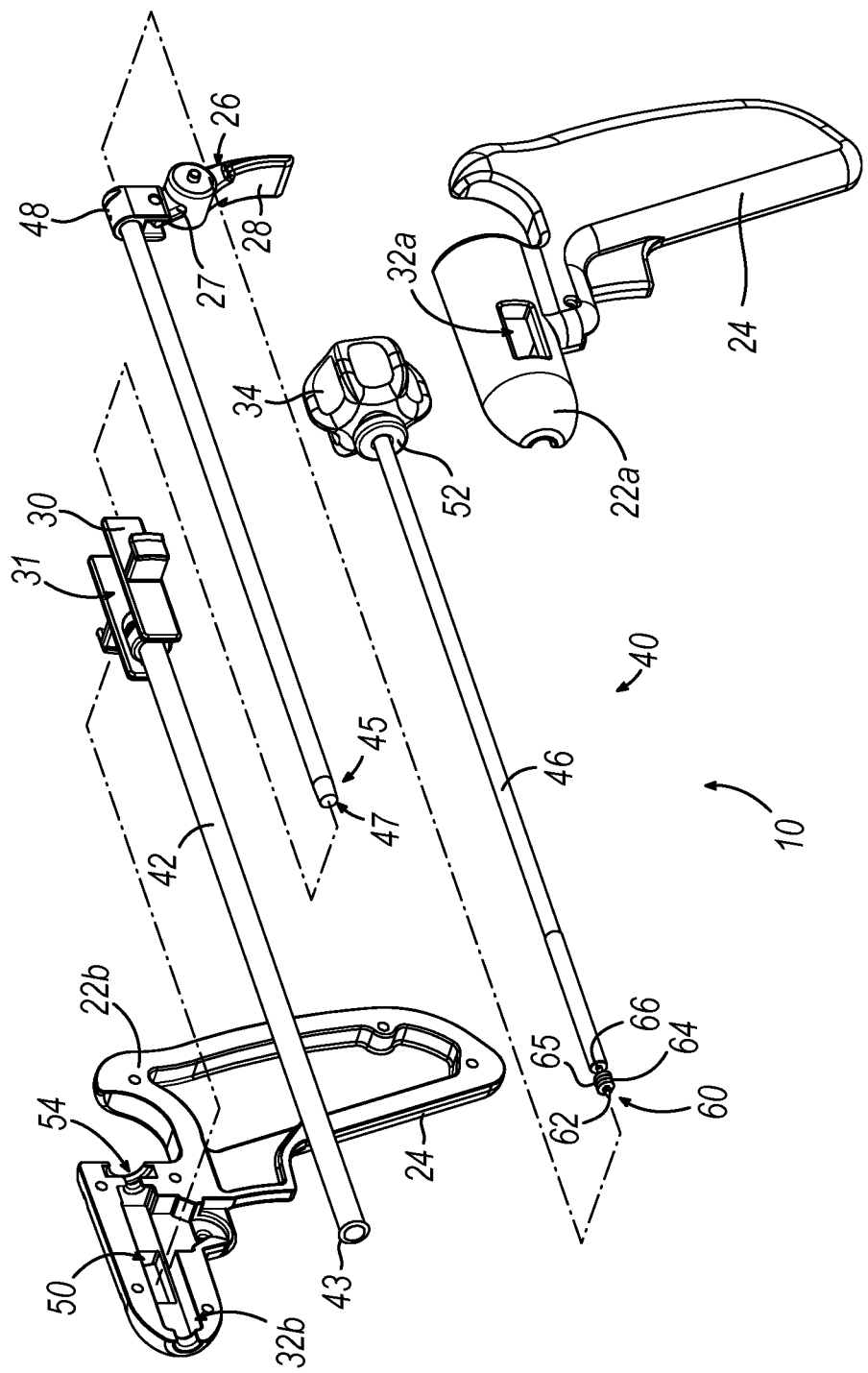
FIG. 5 depicts an exploded perspective view of the instrument of FIG. 2.
Figure 6:
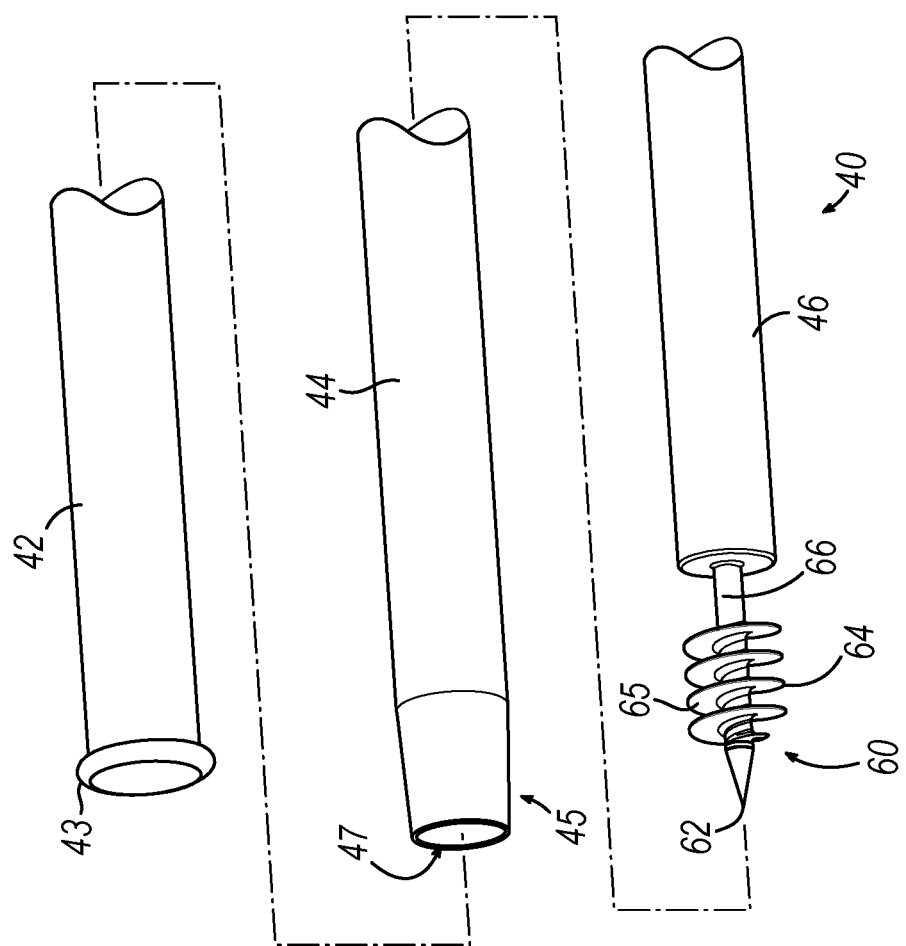
FIG. 6 depicts an exploded perspective view of a shaft assembly of the instrument of FIG. 2.

Shaft assembly (40) extends distally from handle assembly (20). As best seen in FIGS. 5-6, shaft assembly (40) comprises an outer sheath (42), a cutter tube (44), and a rotatable shaft (46). As best seen in FIG. 5, a proximal end of outer sheath (42) is unitarily coupled with a distal portion of sliding trigger (30) such that longitudinal movement of siding trigger (30) causes concurrent longitudinal sliding of outer sheath (42) along longitudinal axis (LA1). Cutter tube (44) is slidably disposed within outer sheath (42) such that cutter tube (44) and outer sheath (42) are able to move independently relative to each other along longitudinal axis (LA1).

Figure 4:
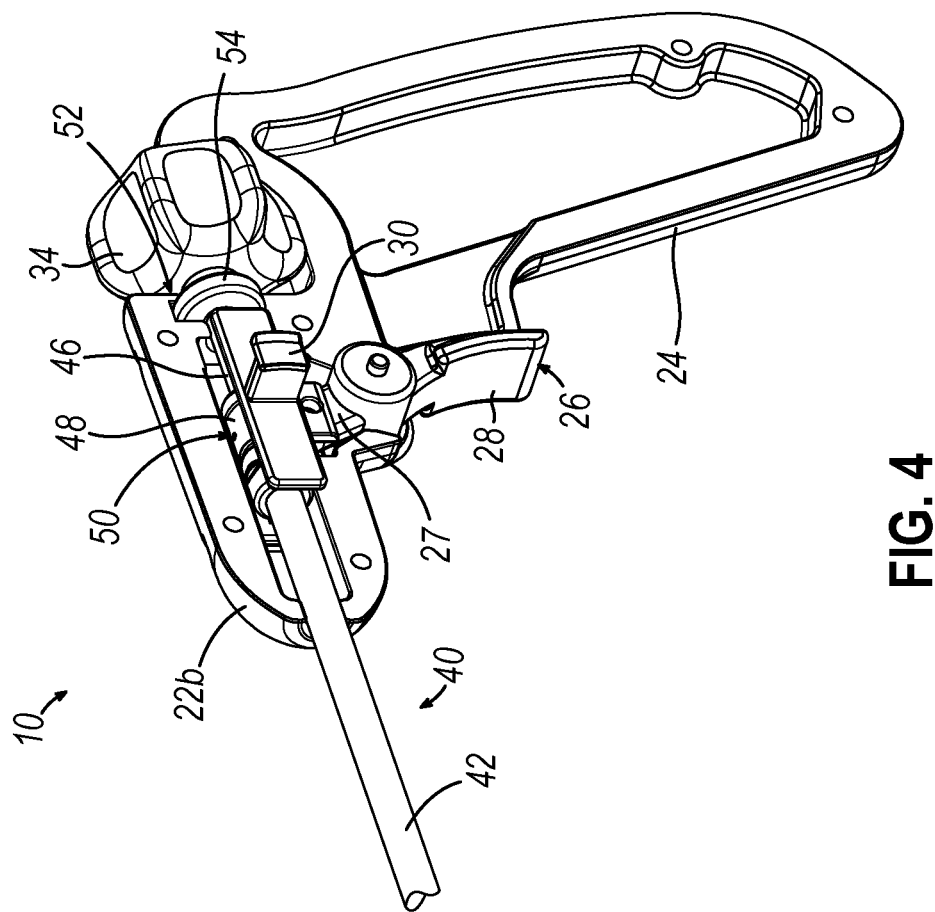
FIG. 4 depicts a detailed perspective view of a handle assembly of the instrument of FIG. 5, with a portion of the handle assembly removed to reveal internal components.

A proximal end of cutter tube (44) is integrally coupled with a sliding member (48). As best seen in FIGS. 4 and 5, sliding member (48) is slidably disposed within a proximal gap (31) defined by sliding trigger (30) such that sliding member (48) slides longitudinally within proximal gap (31) of sliding trigger (30); and such that sliding member (48) and sliding trigger (30) are able to slide longitudinally independently relative to each other. Sliding member (48) is pivotably coupled with an arm (27) extending unitarily from pivoting trigger (26) in an opposite direction of paddle (28). It should therefore be understood that pivoting of paddle (28) toward pistol grip (24) will cause pivoting of arm (27) distally, and vice versa. It should further be understood that, distal pivoting of arm (27) will cause distal longitudinal movement of sliding member (48) and cutter tube (44) along longitudinal axis (LA1); and proximal pivoting of arm (27) will cause proximal longitudinal movement of sliding member (48) and cutter tube (44) along longitudinal axis (LA1).

Rotatable shaft (46) is rotatably disposed within cutter tube (44) such that rotatable shaft (46) rotates independently relative to cutter tube (44) and such that cutter tube (44) is capable of moving longitudinally independently relative to rotatable shaft (46). A proximal end of rotatable shaft (46) is integrally coupled with rotatable knob (34) such that rotation of rotatable knob (34) causes rotation of rotatable shaft (46) about longitudinal axis (LA1). As best seen in FIG. 5, an annular flange (52) extends outwardly from a distal portion of rotatable knob (34) and is rotatably disposed within an annular pocket (54) that is formed in body (22), such that rotatable knob (34) is capable of rotating yet incapable of moving longitudinally relative to longitudinal axis (LA1).

The distal end of outer sheath (42) includes an outwardly projecting annular bumper (43). By way of example only, bumper (43) may be formed of steel, hard plastic, soft plastic, elastomeric material, etc.

A distal portion of cutter tube (44) has a tapered distal region (45) terminating in an opening (47) that is defined by a sharp annular edge. An auger member (60) extends distally from a distal end of rotatable shaft (46) such that as rotatable shaft (46) rotates, auger member (60) rotates as well. Auger member (60) comprises a minor shaft (66) having a sharp distal tip (62) and a helical blade or flight (64) projecting outwardly from minor shaft (66). As will be discussed in more detail below, sharp distal tip (62) may be used to penetrate the sinus wall (SW). The length of sharp distal tip (62) may be configured to avoid inadvertent contact with other portions of sinus wall (SW).

Figure 7:
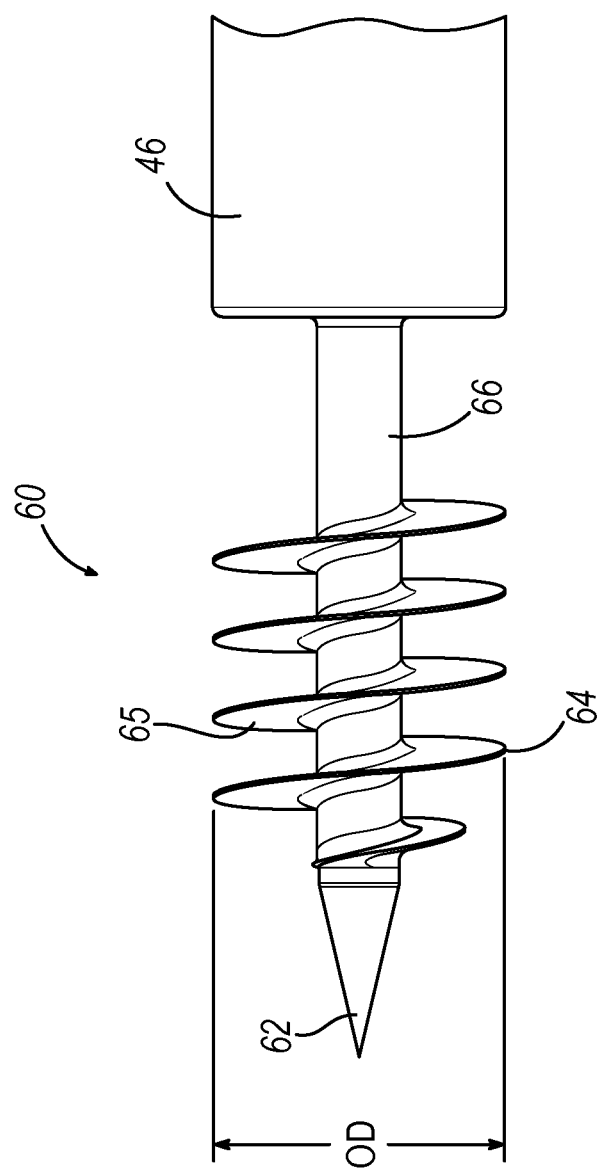
FIG. 7 depicts a detailed side elevational view of an exemplary auger of the shaft assembly of FIG. 5.
Figure 8:
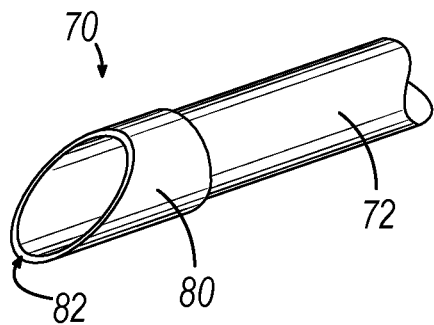
FIG. 8 depicts a perspective view of an exemplary alternative outer sheath assembly that may be used with the instrument of FIG. 2.
Figure 9:
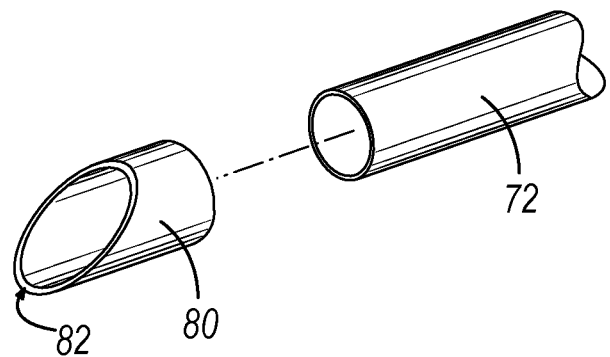
FIG. 9 depicts an exploded view of the outer sheath assembly of FIG. 8.

Helical flight (64) presents an effective outer diameter (OD) that is substantially similar to an inner diameter defined by the sharp annular distal edge of cutter tube (44). In the present example, a gap between the inner diameter defined by the sharp annular distal edge of cutter tube (44) and the effective outer diameter (OD) of helical flight (64) is dimensioned to prevent any tissue from getting lodged between the inner diameter defined by the sharp annular distal edge of cutter tube (44) and the effective outer diameter (OD) of helical flight (64). Also in the present example, the effective outer diameter (OD) is approximately equal to the outer diameter of major diameter proximal portion (86). As best seen in FIG. 7, beginning at a distal portion of helical flight (64), helical flight (64) gradually projects further from outwardly minor shaft (66) until reaching outer diameter (OD).

Auger member (60) of the present example also defines a longitudinal gap extending longitudinally between a proximal end of helical flight (64) and the distal end of rotatable shaft (46). An exterior edge of helical flight (64) in the present example presents a flat surface (65). As will be discussed in more detail below, helical flight (64) is configured to guide and drive auger member (60) through an opening formed in sinus wall (SW) by sharp distal tip (62); and to provide a structural anchor for instrument (10) within sinus wall (SW).

B. Exemplary Retractable Sheath of Instrument

FIGS. 8-11E depict an exemplary alternative sheath assembly (70) that may be readily incorporated into shaft assembly (40) of instrument (10), in place of outer sheath (42). Sheath assembly (70) of this example comprises a tube (72) and a tip member (80) positioned at the distal end (74) of tube (72). Tip member (80) includes a distal edge (82) that defines a plane that is oriented at an oblique angle relative to the longitudinal axis of tube (72). In some instances, the oblique orientation of distal edge (82) may facilitate navigation of shaft assembly (40) through the paranasal cavity. For instance, distal edge (82) may act as a cam, thereby driving anatomical structures out of the way as a lead-in for further insertion of tube (72).

Figure 10A:
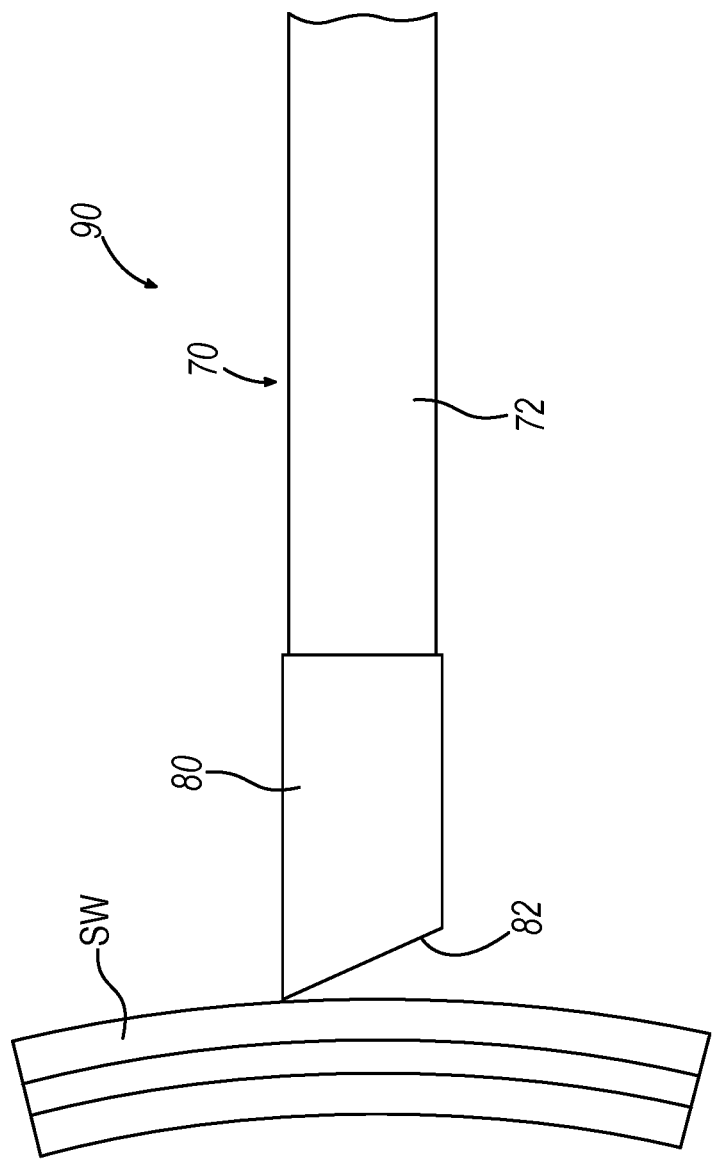
FIG. 10A depicts a side elevational view of the shaft assembly of FIG. 6, incorporating the outer sheath assembly of FIG. 8, with the entire shaft assembly in a first longitudinal position.
Figure 10B:
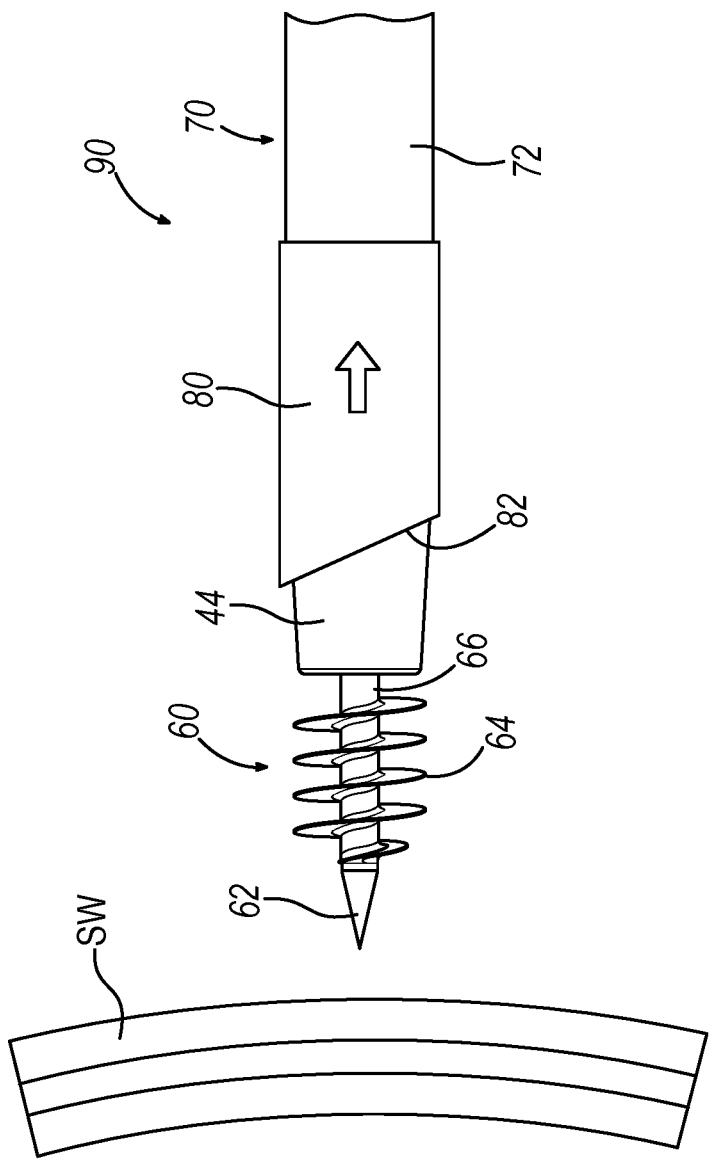
FIG. 10B depicts a side elevational view of the shaft assembly of FIG. 6, incorporating the outer sheath assembly of FIG. 8, with the outer sheath assembly retracted proximally while the rest of the shaft assembly remains in the first longitudinal position.

FIGS. 10A-11E show a shaft assembly (90) that incorporates sheath assembly (70), being used to form an opening in a sinus wall (SW). The sinus wall (SW) may be a wall of the ethmoid bulla (EB) (e.g., the anterior face of the ethmoid bulla (EB)) or the wall of some other sinus cavity. In this example, shaft assembly (90) is identical to shaft assembly (40), except that shaft assembly (90) of this example includes sheath assembly (70) instead of sheath (42). As shown in FIGS. 10A and 11A, shaft assembly (90) is initially positioned such that the distal-most portion of distal edge (82) contacts the sinus wall (SW). Up to this point, auger member (60) and cutter tube (44) are covered by sheath assembly (70). Then, sheath assembly (70) is retracted proximally (e.g., by moving sliding trigger (30) longitudinally proximally), thereby revealing auger member (60) and the distal end of cutter tube (44) as shown in FIGS. 10B and 11B.

Figure 10C:
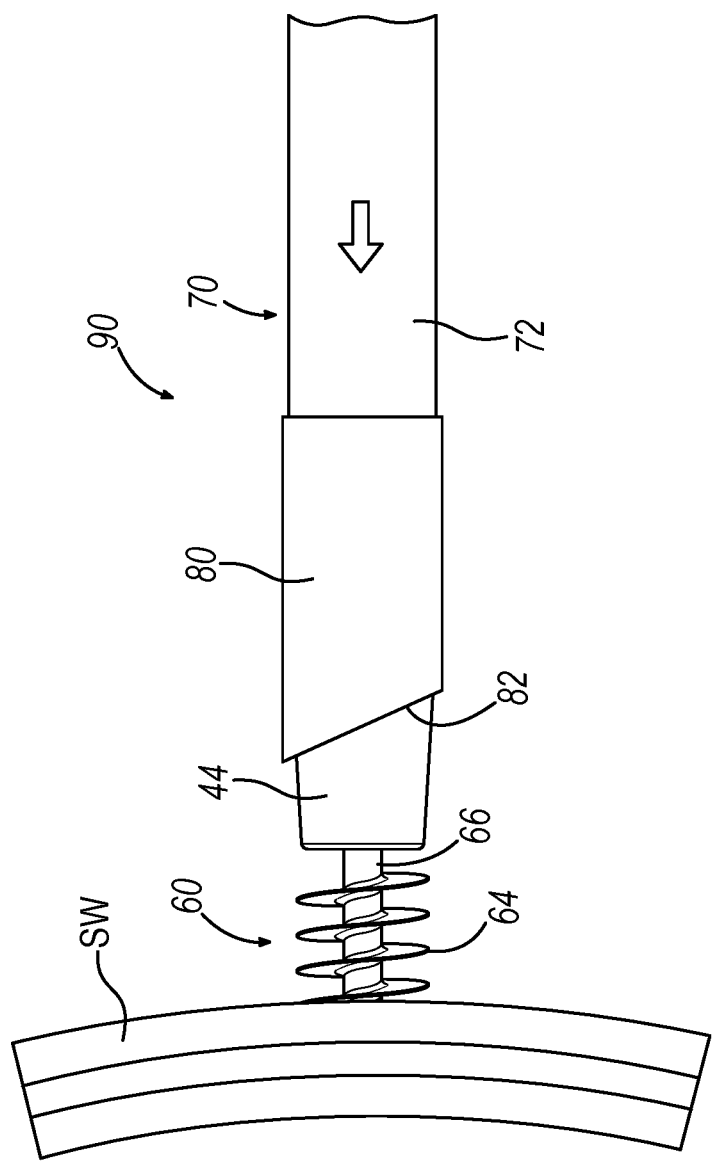
FIG. 10C depicts a side elevational view of the shaft assembly of FIG. 6, incorporating the outer sheath assembly of FIG. 8, with the entire shaft assembly advanced to a second longitudinal position.
Figure 10D:
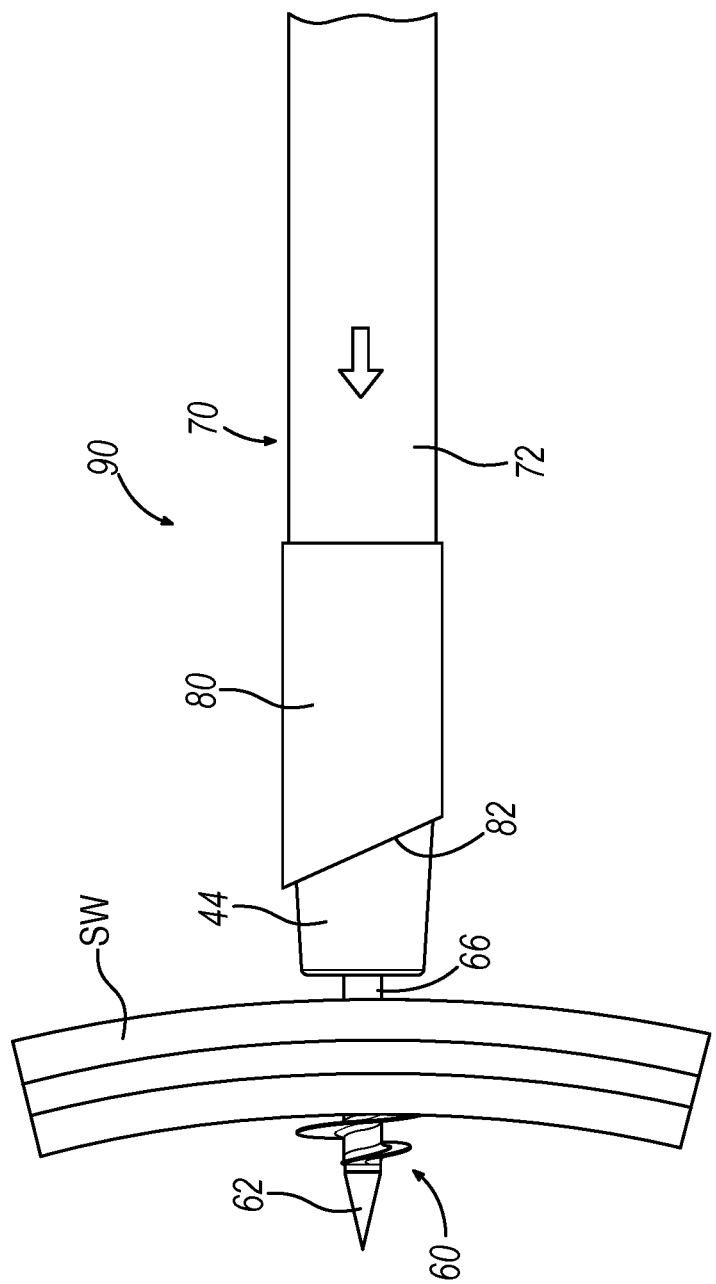
FIG. 10D depicts a side elevational view of the shaft assembly of FIG. 6, incorporating the outer sheath assembly of FIG. 8, with the entire shaft assembly advanced to a third longitudinal position.
Figure 11A:
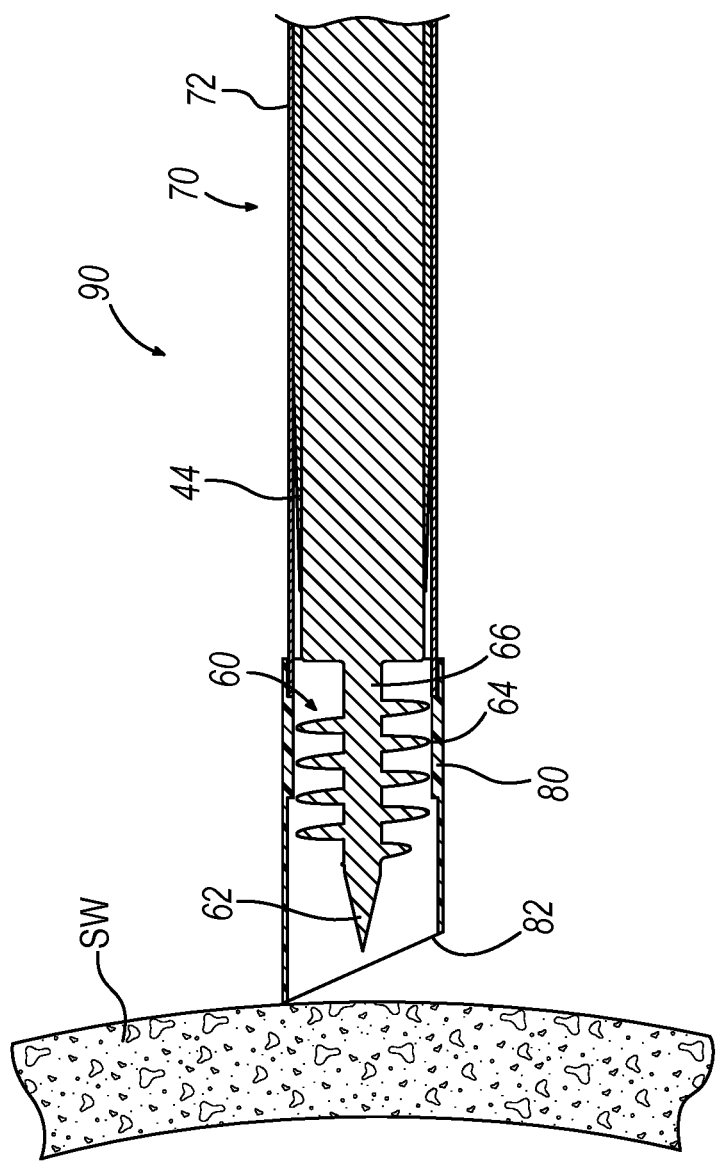
FIG. 11A depicts a side elevational view of the shaft assembly of FIG. 6, incorporating the outer sheath assembly of FIG. 8, with the entire shaft assembly in the first longitudinal position.
Figure 11B:
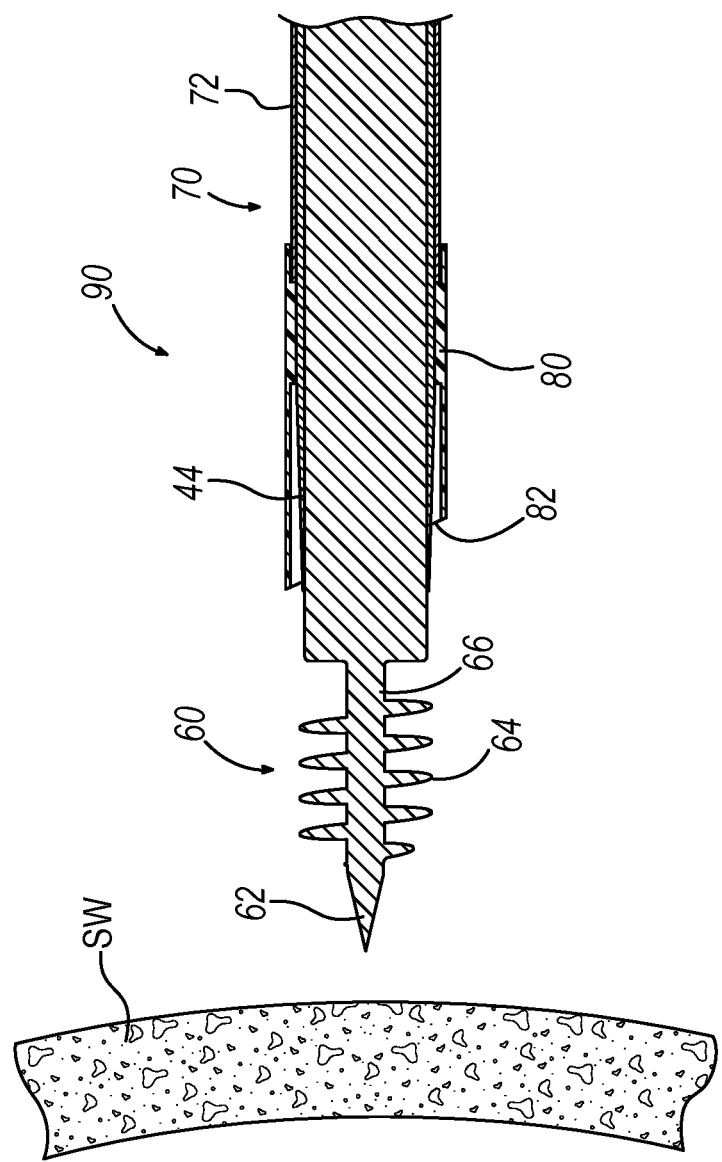
FIG. 11B depicts a side cross-sectional view of the shaft assembly of FIG. 6, incorporating the outer sheath assembly of FIG. 8, with the outer sheath assembly retracted proximally while the rest of the shaft assembly remains in the first longitudinal position.
Figure 11C:
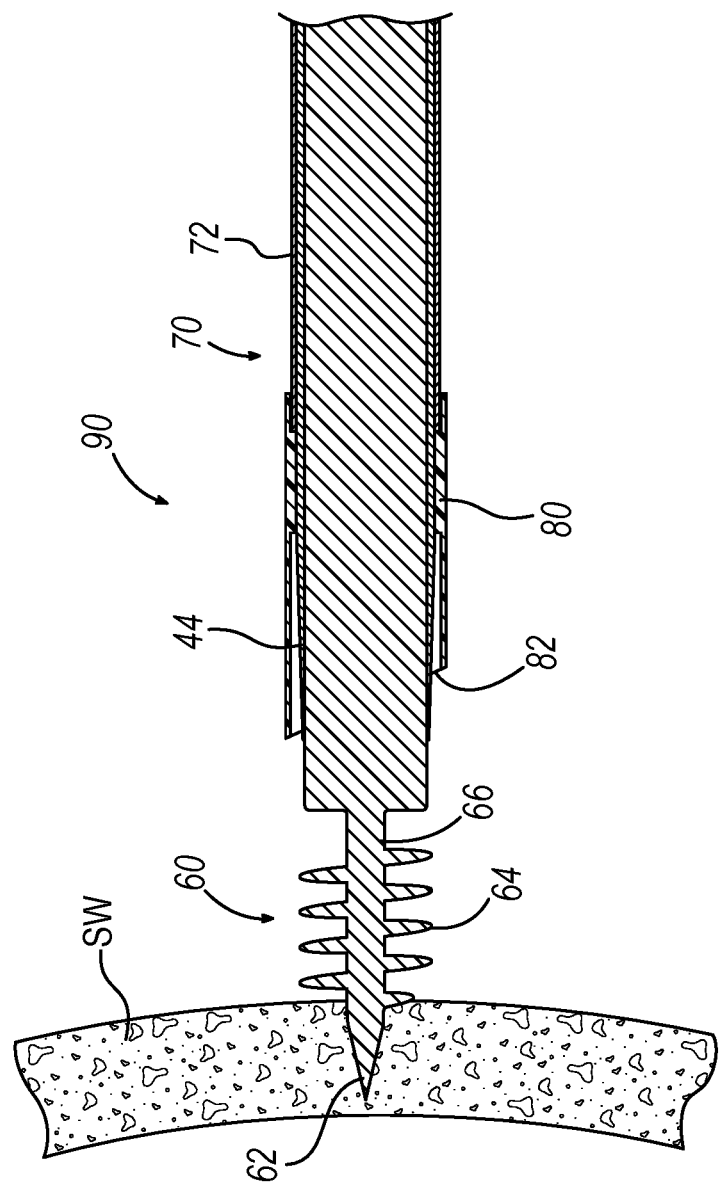
FIG. 11C depicts a side cross-sectional view of the shaft assembly of FIG. 6, incorporating the outer sheath assembly of FIG. 8, with the entire shaft assembly advanced to the second longitudinal position.

With sheath assembly (70) retracted, the entire shaft assembly (90) is advanced distally toward the sinus wall (SW), until sharp distal tip (62) of auger member (60) pierces the sinus wall (SW) as shown in FIGS. 10C and 11C. With tip (62) in the sinus wall (SW), the operator continues to advance the entire shaft assembly (90) while rotating auger member (60) about the longitudinal axis of shaft assembly (90) (e.g., by rotating rotatable knob (34)). It should be understood that, after initially piercing the sinus wall (SW) with sharp distal tip (62), auger member (60) continues to advance distally by rotating due to the helical configuration of flight (64). In particular, helical flight (64) is driven through the sinus wall (SW) like a screw. Auger member (60) eventually reaches the position shown in FIGS. 10D and 11D, where helical flight (64) is located within sinus wall (SW). In some instances, the operator stops rotating auger member (60) and stops advancing the entire shaft assembly (90) at this stage. In other words, the region of minor shaft (66) proximal to flight (64) does not reach the sinus wall (SW) in some instances. In some other instances, the operator rotates auger member (60) and continues to advance the entire shaft assembly (90) until sinus wall (SW) is positioned about the region of minor shaft (66) proximal to flight (64). In either case, it should be understood that auger member (60) may be advanced through the sinus wall (SW) solely due to rotation of auger member (60), such that the operator need not also press distally on any portion of instrument (10) as flight (64) traverses the sinus wall (SW).

Figure 10E:
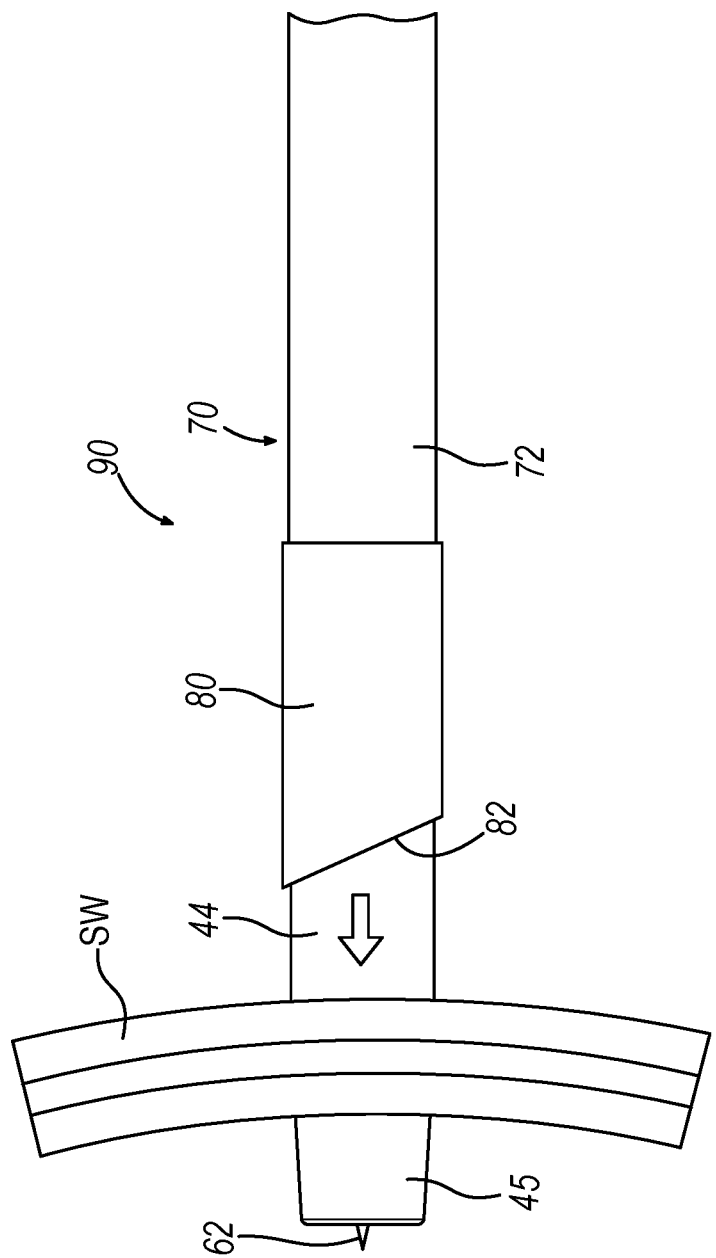
FIG. 10E depicts a side elevational view of the shaft assembly of FIG. 6, incorporating the outer sheath assembly of FIG. 8, with the cutter advanced distally while the rest of the shaft assembly remains in the third longitudinal position.
Figure 11D:
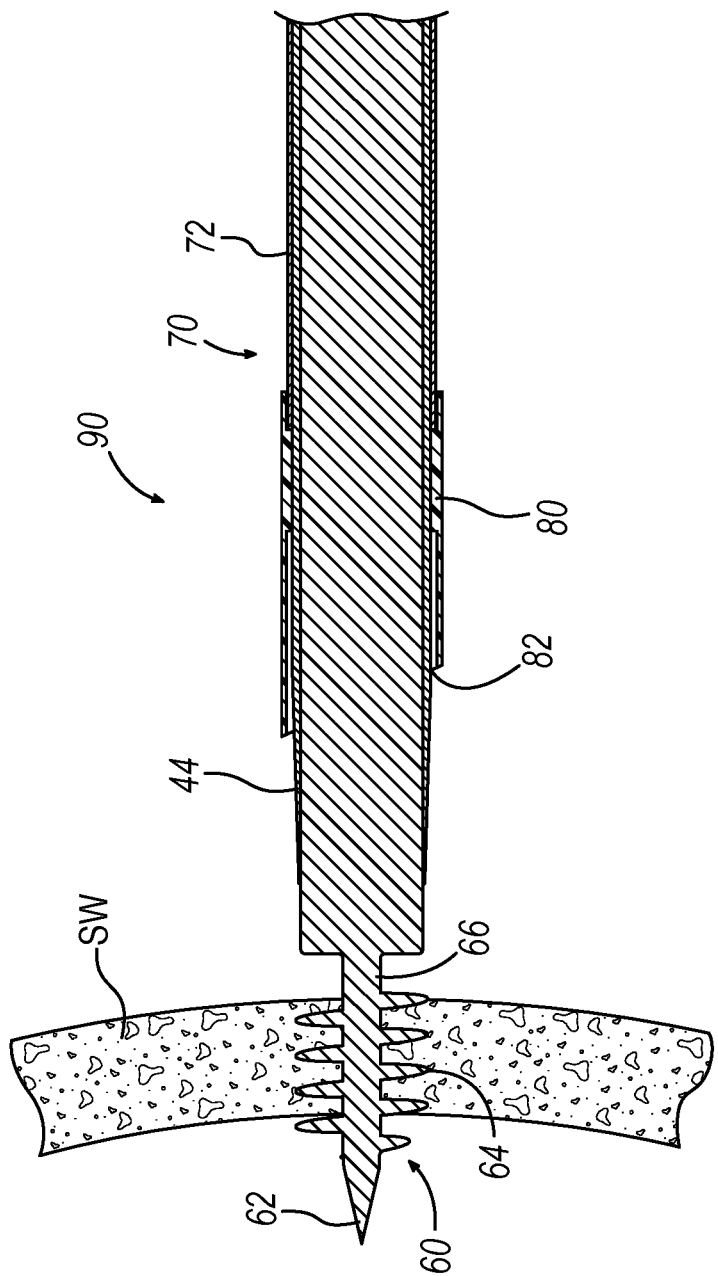
FIG. 11D depicts a side cross-sectional view of the shaft assembly of FIG. 6, incorporating the outer sheath assembly of FIG. 8, with the entire shaft assembly advanced to the third longitudinal position.
Figure 11E:
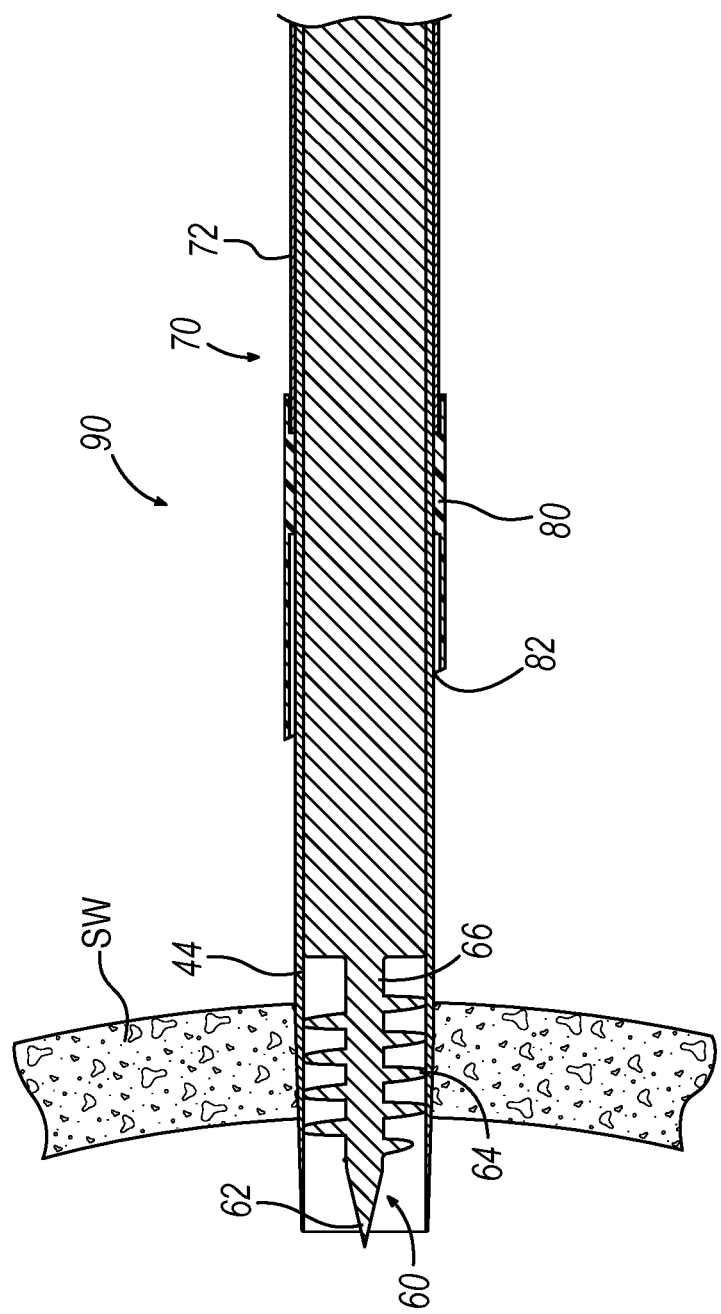
FIG. 11E depicts a side cross-sectional view of the shaft assembly of FIG. 6, incorporating the outer sheath assembly of FIG. 8, with the cutter advanced distally while the rest of the shaft assembly remains in the third longitudinal position.
Figure 11F:
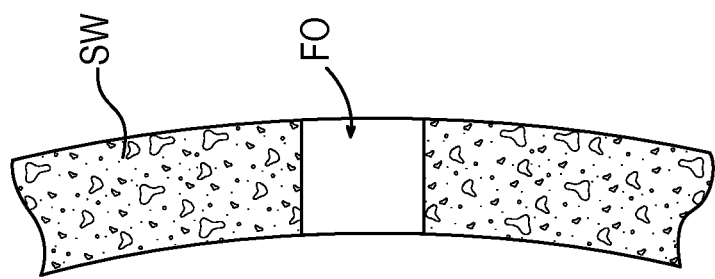
FIG. 11F depicts a side cross-sectional view of a sinus wall with an opening formed by the shaft assembly of FIG. 5.

Having reached the stage shown in FIGS. 10D and 11D, the operator advances cutter tube (44) distally (e.g., by squeezing of pivoting trigger (26) toward pistol grip (24)) while holding the remainder of shaft assembly (90) stationary. Cutter tube (44) thereby cuts a circular opening in the sinus wall (SW), slicing through the bone and tissue of the sinus wall (SW), as shown in FIGS. 10E and 11E. During this advancement of cutter tube (44), auger member (60) anchors shaft assembly (90) in the sinus wall (SW) and may further provide structural support to the sinus wall (SW) as cutter tube (44) traverses the sinus wall (SW). After cutter tube (44) cuts through the sinus wall (SW), the entire shaft assembly (90) is retracted proximally to reveal the formed opening (FO) in the sinus wall (SW), as shown in FIG. 11F. Shaft assembly (90) may then be cleaned, disposed of, or otherwise handled. Merely illustrative ways in which auger member (60) may be cleaned will be described in greater detail below, while other examples will be apparent to those of ordinary skill in the art in view of the teachings herein.

While the foregoing example describes the use of instrument (10) to form an opening through a sinus wall (SW), instrument (10) may be similarly used in various other kinds of procedures, including but not limited to procedures where instrument (10) is used to reduce the volume of one or more turbinates (LT, MT, UT).

II. Exemplary Image Guided Surgery Navigation System

Figure 12:
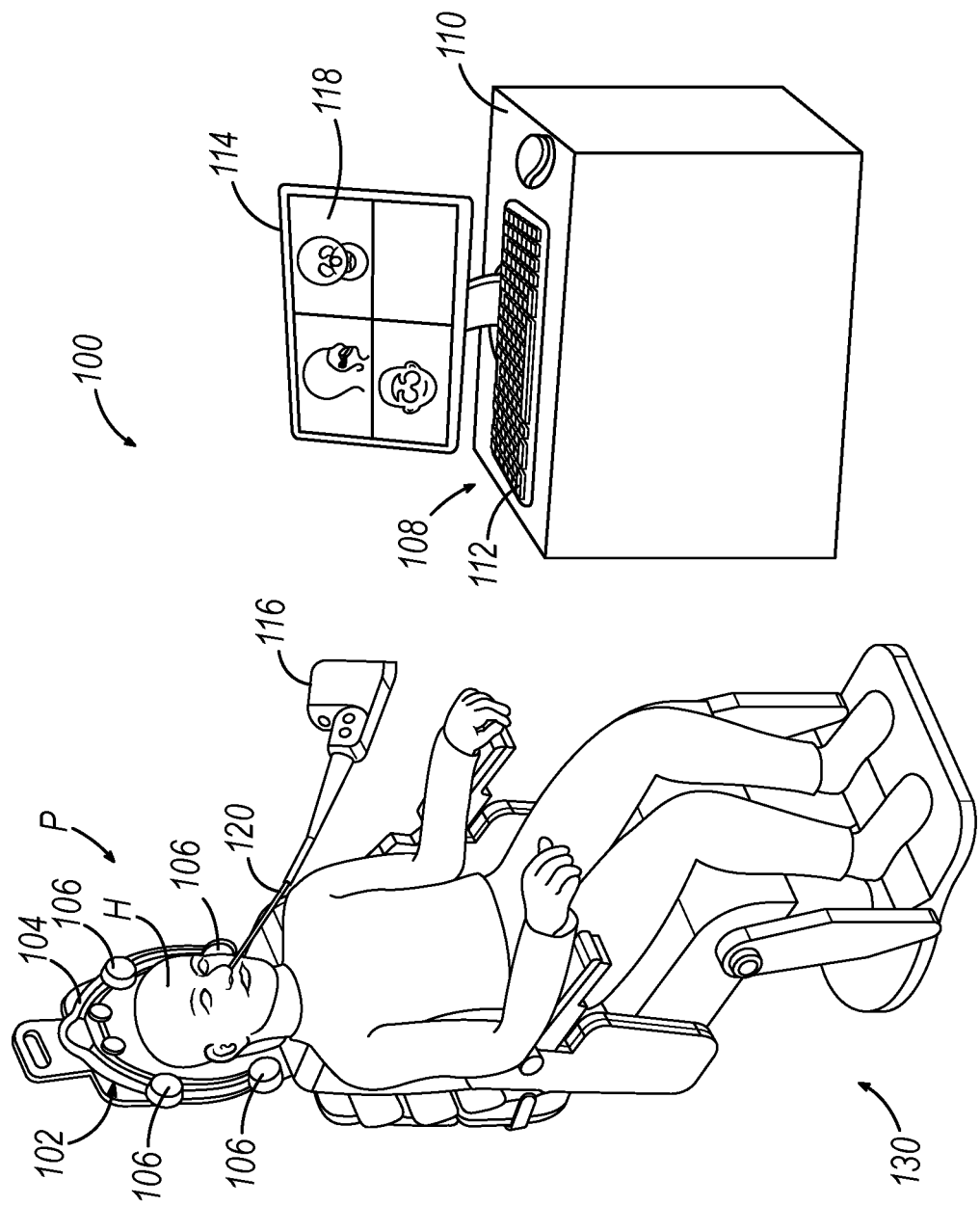
FIG. 12 depicts a perspective view of an exemplary image-guided surgical navigation system for tracking the position of an instrument within a patient.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 12 shows an exemplary IGS navigation system (100) enabling an ENT procedure to be performed using image guidance. In addition to or in lieu of having the components and operability described herein IGS navigation system (100) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (100) of the present example comprises a field generator assembly (102), which comprises magnetic field generators (106) that are integrated into a horseshoe-shaped frame (104). Field generators (106) are operable to generate alternating magnetic fields of different frequencies around the head (H) of the patient (P). A navigation guidewire (120) is inserted into the head (H) of the patient (P) in this example. Navigation guidewire (120) may be a standalone device or may be positioned on an end effector or other location of a medical instrument such as a surgical cutting instrument or dilation instrument. In the present example, frame (104) is mounted to a chair (130), with the patient (P) being seated in the chair (130) such that frame (104) is located adjacent to the head (H) of the patient (P). By way of example only, chair (130) and/or field generator assembly (102) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein.

IGS navigation system (100) of the present example further comprises a processor (108), which controls field generators (106) and other elements of IGS navigation system (100). For instance, processor (108) is operable to drive field generators (106) to generate alternating electromagnetic fields; and process signals from navigation guidewire (120) to determine the location of a sensor in navigation guidewire (120) within the head (H) of the patient (P). Processor (108) comprises a processing unit communicating with one or more memories. Processor (108) of the present example is mounted in a console (110), which comprises operating controls (112) that include a keypad and/or a pointing device such as a mouse or trackball. A physician uses operating controls (112) to interact with processor (108) while performing the surgical procedure.

Navigation guidewire (120) includes a sensor (not shown) that is responsive to positioning within the alternating magnetic fields generated by field generators (106). A coupling unit (116) is secured to the proximal end of navigation guidewire (120) and is configured to provide communication of data and other signals between console (110) and navigation guidewire (120). Coupling unit (116) may provide wired or wireless communication of data and other signals between console (110) and navigation guidewire (120).

In the present example, the sensor of navigation guidewire (120) comprises at least one electrically conductive coil at the distal end of navigation guidewire (120). When such a coil is positioned within an alternating electromagnetic field generated by field generators (106), the alternating magnetic field may generate electrical current in the coil, and this electrical current may be communicated proximally along the electrical conduit(s) in navigation guidewire (120) and further to processor (108) via coupling unit (116). This phenomenon may enable IGS navigation system (100) to determine the location of the distal end of navigation guidewire (120) or other medical instrument (e.g., dilation instrument, surgical cutting instrument, etc.) within a three-dimensional space (i.e., within the head (H) of the patient (P), etc.). To accomplish this, processor (108) executes an algorithm to calculate location coordinates of the distal end of navigation guidewire (120) from the position-related signals of the sensor coil(s) in navigation guidewire (120). While the position sensor is located in guidewire (120) in this example, such a position sensor may be integrated into various other kinds of instruments, including those described in greater detail below.

Processor (108) uses software stored in a memory of processor (108) to calibrate and operate IGS navigation system (100). Such operation includes driving field generators (106), processing data from navigation guidewire (120), processing data from operating controls (112), and a driving display screen (114). In some implementations, operation may also include monitoring and enforcement of one or more safety features or functions of IGS navigation system (100). Processor (108) is further operable to provide video in real time via display screen (114), showing the position of the distal end of navigation guidewire (120) in relation to a video camera image of the patient's head (H), a CT scan image of the patient's head (H), and/or a computer generated three-dimensional model of the anatomy within and adjacent to the patient's nasal cavity. Display screen (114) may display such images (118) simultaneously and/or superimposed on each other during the surgical procedure. Such displayed images (118) may also include graphical representations of instruments that are inserted in the patient's head (H), such as navigation guidewire (120), such that the operator may view the virtual rendering of the instrument at its actual location in real time. By way of example only, display screen (114) may provide images (118) in accordance with at least some of the teachings of U.S. Pat. No. 10,463,242, entitled "Guidewire Navigation for Sinuplasty," issued Nov. 5, 2019, the disclosure of which is incorporated by reference herein. In the event that the operator is also using an endoscope, the endoscopic image may also be provided on display screen (114).

The images (118) provided through display screen (114) may help guide the operator in maneuvering and otherwise manipulating instruments within the patient's head (H) when such instruments incorporate navigation guidewire (120). It should also be understood that other components of a surgical instrument and other kinds of surgical instruments, as described below, may incorporate a sensor like the sensor of navigation guidewire (120).

III. Exemplary Piercing Instrument Having Navigation Sensor

Figure 13:
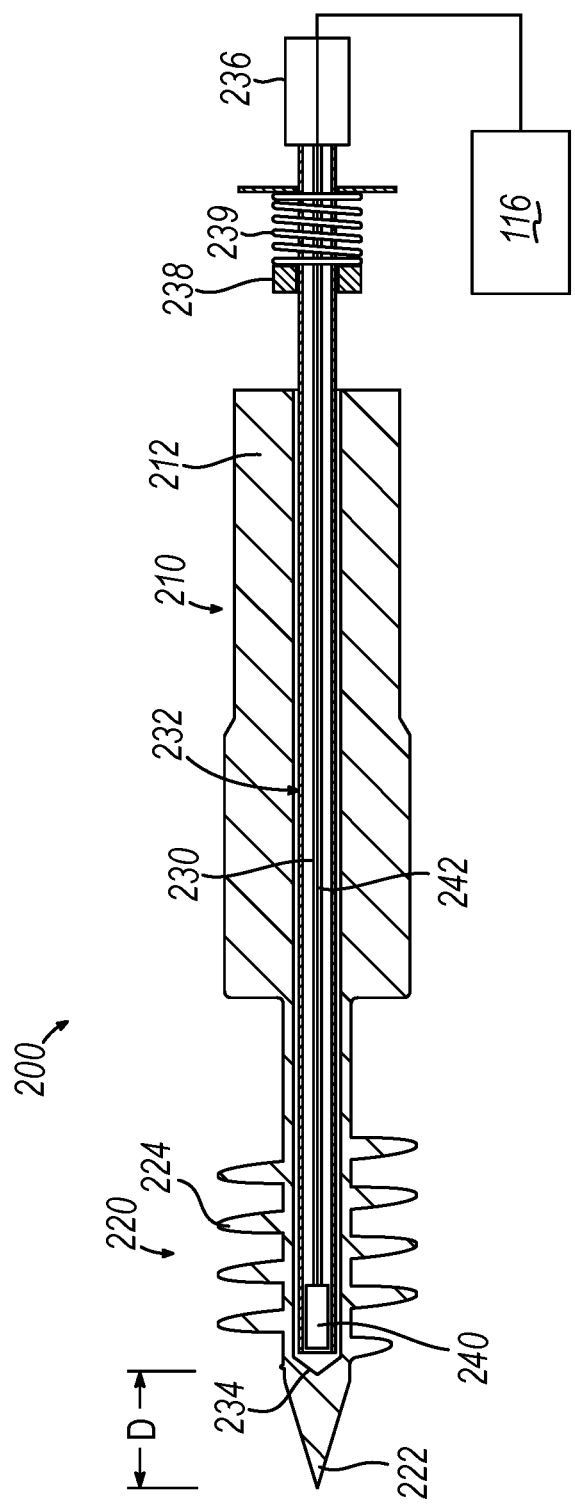
FIG. 13 depicts a schematic side sectional view of a distal portion of another exemplary surgical piercing instrument having an electromagnetic navigation sensor configured for use with the navigation system of FIG. 12.

In some instances, it may be desirable to enable a user to track a position of the distal end of piercing instrument (10) described above in real-time during a surgical procedure, without direct visualization via an endoscope. FIG. 13 shows an exemplary alternative piercing instrument (200) that includes a navigation sensor (240) operable in conjunction with navigation system (100) to provide such tracking in a manner similar to that described above in connection with navigation guidewire (120). It will be appreciated that piercing instrument (200) is similar in structure and function to piercing instrument (10) described above as except as otherwise described below.

As shown in FIG. 13, piercing instrument (200) includes a shaft assembly (210) that includes a rotatable shaft (212), a cutter tube (214) (see FIG. 14) slidably disposed over rotatable shaft (212), and an outer sheath (216) (see FIG. 14) slidably disposed over cutter tube (214). Similar to rotatable shaft (46), the distal end of rotatable shaft (212) includes a cutting member in the form of an auger member (220) having a sharp distal tip (222) and a helical blade (224) (or "flight") arranged proximal to the shaft distal tip (222). Shaft assembly (210) of the present example further includes a cylindrical core rod (230) that extends longitudinally within a bore (232) formed along the central axis of rotatable shaft (212). Central bore (232) has a closed distal end (234) aligned with the distal end of helical blade (224) and the proximal end of sharp distal tip (222). Central bore (232) may open to a proximal end of rotatable shaft (212) such that a proximal end of core rod (230) protrudes proximally from rotatable shaft (212) and couples to handle assembly (20) independently from rotatable shaft (212).

In the present version, the proximal end of core rod (230) is coupled to handle assembly (20) with a rail mechanism (236) that constrains core rod (230) rotationally relative to handle assembly (20) while permitting core rod (230) to translate axially within central bore (232) and relative to handle assembly (20). In that regard, rail mechanism (236) may interface with handle assembly (20) with one of more rail-like protrusions and corresponding elongate channels (not shown) in which the rail-like protrusions are configured to translate. A proximal portion of core rod (230) includes an annular flange (238) against which the dial end of a resilient member in the form of a compression spring (239) is anchored. A proximal end of compression spring (239) is anchored against a feature of handle assembly (20) such that compression spring (239) biases core rod (230) distally within central bore (232) of rotatable shaft (212). In this manner, the distal end of core rod (230) is maintained at the distal end of core rod (230). Meanwhile, rotatable shaft (212) is permitted to rotate coaxially about core rod (230), which remains rotationally fixed relative to handle assembly (20).

A navigation sensor (240) is housed within the distal end of core rod (230) and is configured to communicate with processor (108) of surgical navigation system (100) to enable live tracking of the position of auger member (220) within a patient during a surgical procedure. In particular, navigation sensor (240) is in the form of an electromagnetic coil configured to generate an electrical signal in response to presence of sensor (240) within the alternating electromagnetic field generated by field generators (106) about head (H) of patient (P), as shown in FIG. 12. Navigation sensor (240) communicates this signal proximally along a sensor wire (242) that couples to communication unit (116). As described above, communication unit (116) may communicate with processor (108) via a wireless or a wired connection. In turn, processor (108) interprets the signals received from coupling unit (116) to display a position of navigation sensor (240), and thus auger member (220), on the preoperative images (118) shown on display screen (114).

In the present example, the distal bias force imparted by compression spring (239) on annular flange (238) of core rod (230) ensures that navigation sensor (240) remains consistently positioned at the distal end of central bore (232) within rotatable shaft (212). Accordingly, as shown in FIG. 13, navigation sensor (240) of the present version is maintained in longitudinal alignment with a distal portion of helical blade (224) at a known axial distance (D) from the distal-most end of sharp distal tip (222). Accordingly, the signals generated by navigation sensor (240) may be interpreted by processor (108) to track a precise location within patient (P) of the distal-most end of sharp distal tip (222) as well as any portion of helical blade (224). A user may thus consult display screen (114) of navigation system (100) to determine a precise depth to which helical blade (224) has been driven into an anatomical structure during a surgical procedure. Advantageously, housing navigation sensor (240) and sensor wire (242) within core rod (230) serves to protect navigation sensor (240) and sensor wire (242) during rotation of rotatable shaft (212) relative to handle assembly (20).

Figure 14:
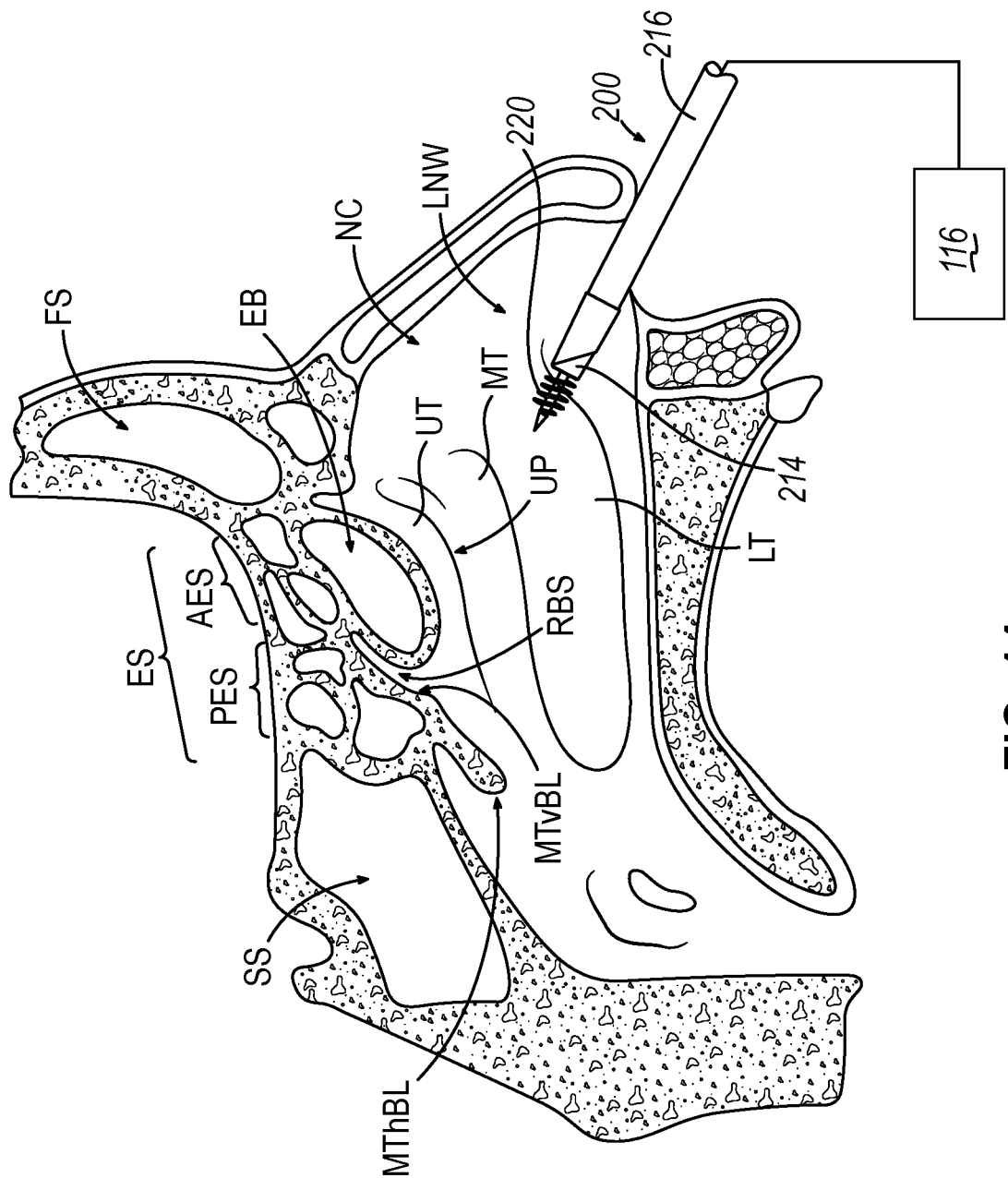
FIG. 14 depicts a left sagittal cross-sectional view of a portion of a human head, showing instrument of FIG. 13 being inserted into the nasal cavity for a surgical procedure under guidance provided by the navigation sensor.

FIG. 14 shows an exemplary deployment of the distal end of piercing instrument (200) within the nasal cavity (NC) of a patient to perform a tissue/bone cutting and removal procedure with real-time tracking of auger member (220) provided by navigation sensor (240) described above. Piercing instrument (200) may be deployed to cut and remove tissue/bone from a variety of wall structures within nasal cavity (NC). For instance, piercing instrument may be deployed to remove tissue/bone from any one or more of the lower turbinate (LT), the middle turbinate (MT), or the upper turbinate (UT) disposed on each lateral nasal wall (LNW) of the nasal cavity (NC). Such a procedure may be performed to reduce turbinate size and thereby improve air flow through the nasal passage, while minimizing unwanted collateral damage to surrounding tissue structures. As described above, location tracking of auger member (220) provided by navigation sensor (240) enables the user to precisely position and embed auger member (220) distally into the targeted wall structure at a desired depth for removing tissue/bone, via subsequent distal actuation of cutter tube (214) over auger member (220). It will be appreciated that piercing instrument (200) may be deployed at a variety of other sites within nasal cavity (NC), or within other body cavities of patient (P), to remove tissue/bone with the location tracking assistance provided by navigation sensor (240) and navigation system (100).

IV. Exemplary Additional Features for Surgical Piercing Instrument

It may be desirable to provide either of surgical piercing instruments (10, 200) described above with additional features to improve precision and usability of instrument (10, 200) during a surgical procedure. It will be appreciated that any one or more of the exemplary features described below in connection with FIGS. 15-20 may be integrated into either of instruments (10, 200) described above. Moreover, it will be understood that the exemplary instruments and components described below are similar to the corresponding instruments (10, 200) and components described above, except as otherwise noted.

A. Exemplary Motor-Powered Handle Assembly

Figure 15:
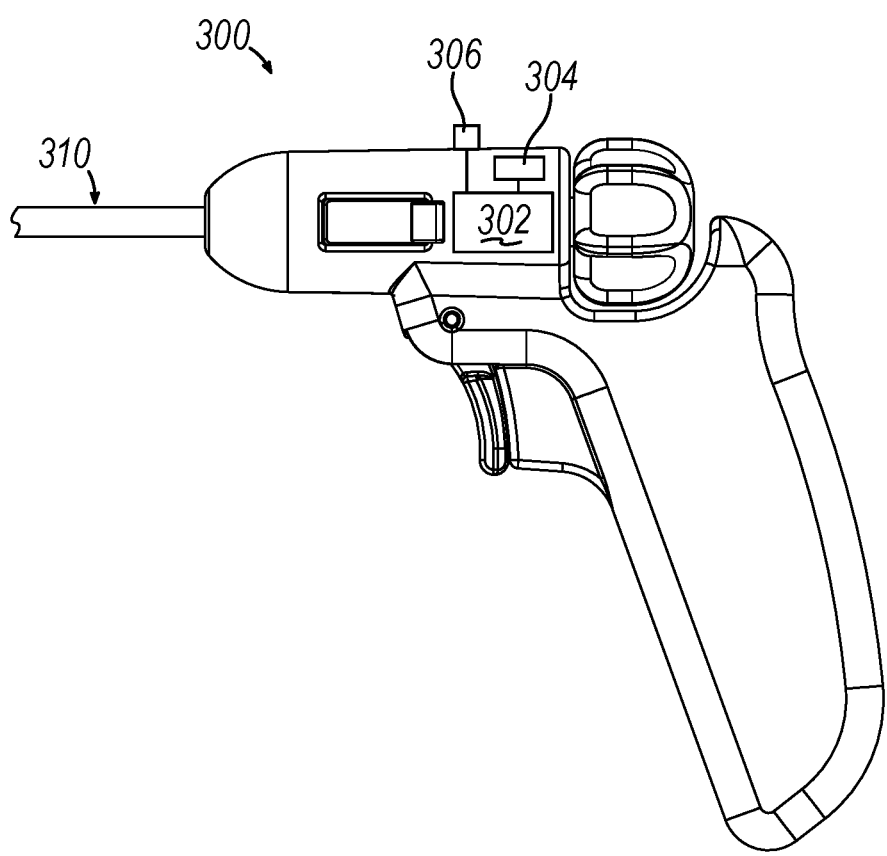
FIG. 15 depicts a side elevation view of a handle assembly of another exemplary surgical piercing instrument having a motor.

FIG. 15 shows an exemplary alternative handle assembly (300) suitable for use in place of handle assembly (20) described above. Handle assembly (300) is similar to handle assembly (20) except that handle assembly (300) houses a motor (302) that is operatively coupled with and configured to actuate one or more components of shaft assembly (310). For instance, motor (302) may be configured to drive rotation of a rotatable shaft (not shown) similar to rotatable shafts (46, 212), and/or translation of a cutter tube (not shown) similar to cutter tube (44). In some such versions, actuation by motor (302) may be fully automated based on feedback provided by one or more sensors (not shown) provided within or on handle assembly (300) and/or shaft assembly (310). For instance, motor (302) may be configured to automatically transition from driving rotation of rotatable shaft (46, 212) to driving translation of cutter tube (44) in response to an encoder detecting that rotatable shaft (46, 212) has completed a predetermined number of revolutions. Alternatively, handle assembly (300) may include a pair of user input elements (306), such as first and second buttons, configured to be independently actuated by the user to initiate rotation of rotatable shaft (46, 212) and subsequently translation of cutter tube (44), respectively.

In versions in which handle assembly (300) includes a single motor (302) operable to drive rotation of rotatable shaft (46, 212) and translation of cutter tube (44), handle assembly (300) may further include a clutch mechanism (not shown) operable to interchangeably engage rotatable shaft (46, 212) and cutter tube (44). In other versions, handle assembly (300) may include separate dedicated motors (302) for driving rotation of rotatable shaft (46, 212) and translation of cutter tube (44), respectively. In other versions, handle assembly (300) may include a single motor (302) operable to drive one of rotatable shaft (46, 212) or cutter tube (44), while the other component is actuated manually.

Handle assembly (300) may further include an internal power source (304) in the form of a battery pack configured to power motor (302), and which may include one or more batteries of any suitable type. In some versions, battery pack (304) may be selectively removed from handle assembly (300) and recharged for multiple uses. In other versions, battery pack (304) may be permanently integrated within handle assembly (300) such that handle assembly (300) is configured to be discarded upon depletion of battery pack. In other versions, battery pack (304) may be omitted and handle assembly (300) may be configured to couple to an external power source with a power cable (not shown), which may be selectively releasable from handle assembly (300) and/or the external power source.

As shown in FIG. 15, handle assembly (300) of the present example further includes one or more actuatable input elements (306) electrically coupled with motor (302) and power source (304), and which is configured to selectively control delivery of electrical power to motor (302) from power source (304) and/or a direction of rotation of motor (302). For instance, in some versions actuatable input element (306) may include a first input element configured to control delivery of power to motor (302), and a second input element configured to control direction of rotation of motor (302). As described above, in some versions input element (306) may include a pair of input elements configured to independently control actuation by motor (302) of a rotatable shaft (46, 212) and a cutter tube (44) of shaft assembly (310). Input element (306) may be in the form of a switch, dial, slide, or any other suitable type of input element apparent to one of ordinary skill in the art in view of the teachings herein.

B. Exemplary Ultrasonic Energy Delivery Features

Figure 16:
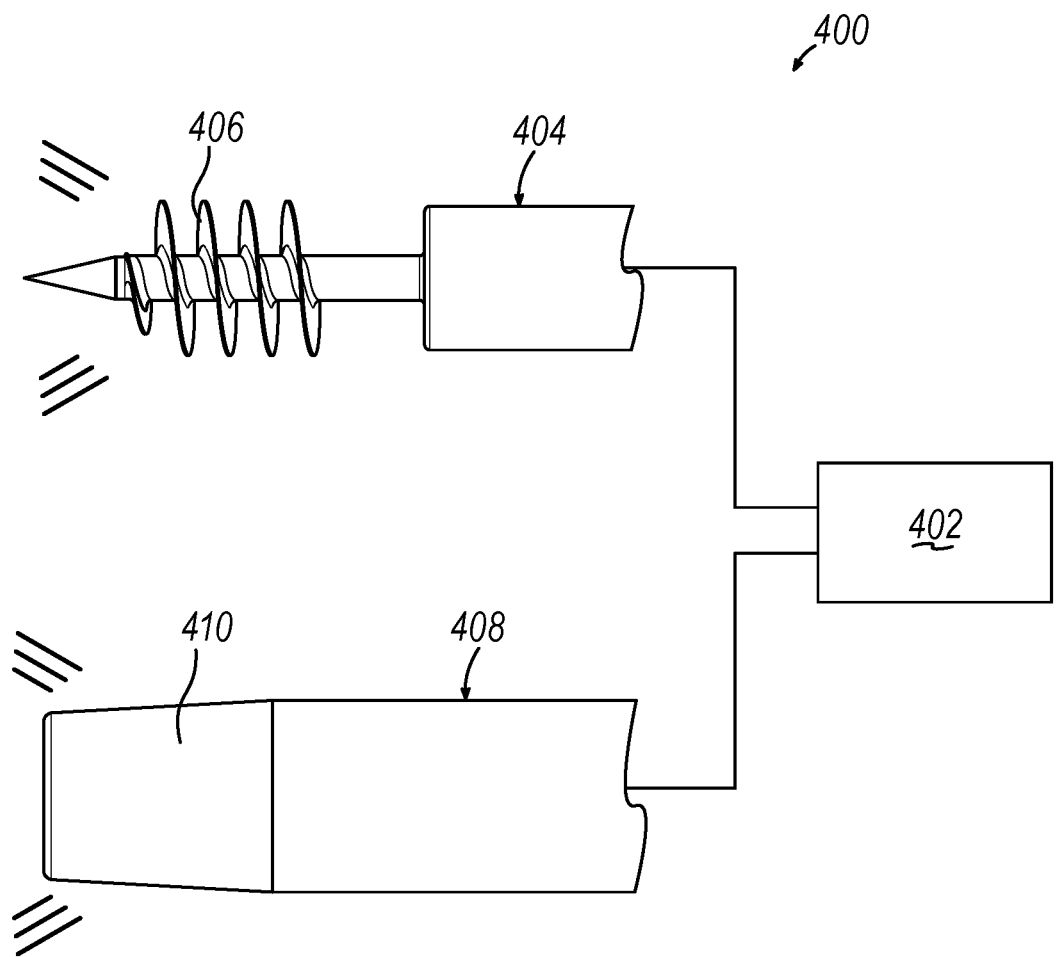
FIG. 16 depicts a schematic side elevation view of distal shaft portions of another exemplary surgical piercing instrument configured to deliver ultrasonic energy at a surgical site.

FIG. 16 shows portions of another exemplary surgical piercing instrument (400) that includes an ultrasonic transducer (402), which may be housed within or otherwise supported by a handle assembly (not shown). Ultrasonic transducer (402) is acoustically coupled with one or both of rotatable shaft (404) and cutter tube (408) such that ultrasonic transducer (402) is operable to drive auger member (406) of rotatable shaft (404) or tapered distal region (410) of cutter tube (408) with ultrasonic energy. Such ultrasonic energy is then delivered from auger member (406) and tapered distal region (410) to tissue/bone to provide precise cutting and controlled coagulation of during a surgical procedure. In particular, the ultrasonic energy cuts and coagulates by vibrating auger member (406) and/or tapered distal region (410) at frequencies of approximately 50 kilohertz (kHz), for example, to denature protein in the tissue to form a sticky coagulum. Pressure exerted on the tissue with auger member (406) and/or tapered distal region (410) then collapses blood vessels and allows the coagulum to form a hemostatic seal. The precision of cutting and coagulation may be controlled by the surgeon's technique and adjusting a power level of ultrasonic transducer (402) and/or the manner in which auger member (406) and tapered distal region (410) contacts the targeted tissue/bone.

It will be appreciated that such ultrasonic energy delivery features of instrument (400) may be further configured in accordance with any one or more teachings of U.S. Pat. No. 8,461,744, entitled "Rotating Transducer Mount for Ultrasonic Surgical Instruments," issued Jun. 11, 2013; U.S. Pat. No. 8,591,536, entitled "Ultrasonic Surgical Instrument Blades," issued Nov. 26, 2013; U.S. Pat. No. 8,623,027, entitled "Ergonomic Surgical Instruments," issued Jan. 7, 2014; U.S. Pat. No. 9,095,367, entitled "Flexible Harmonic Waveguides/Blades for Surgical Instruments," issued Aug. 4, 2015; and/or U.S. Pat. No. 9,750,521, entitled "Ultrasonic Blade Overmold," issued Sep. 5, 2017. The disclosure of each of these references is incorporated by reference herein.

C. Exemplary RF Energy Delivery Features

Figure 17:
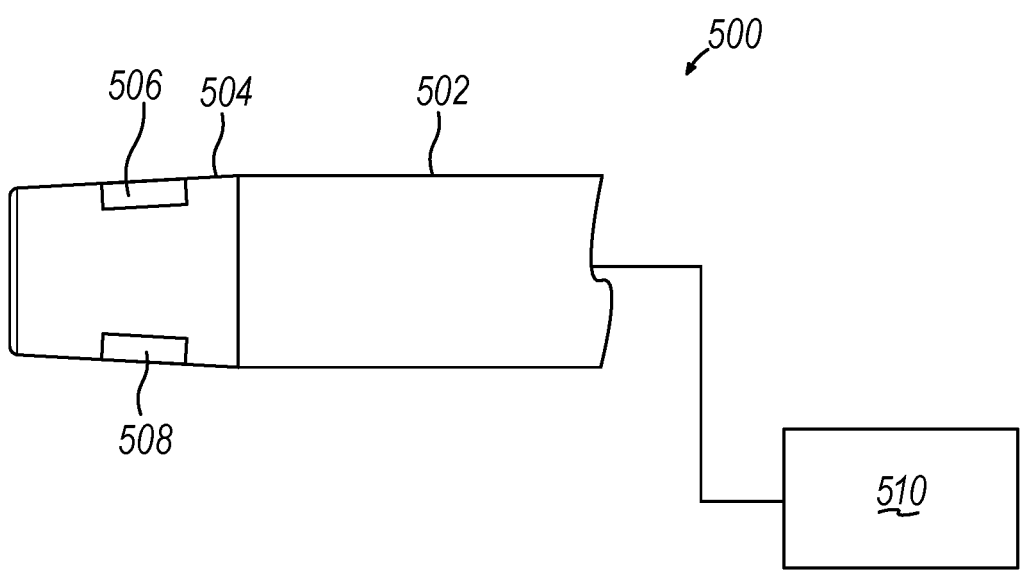
FIG. 17 depicts a schematic side elevation view of a distal shaft portion of another exemplary surgical piercing instrument configured to delivery RF energy at a surgical site.

FIG. 17 shows portions of another exemplary surgical piercing instrument (500) that includes a cutter tube (502) having a tapered distal region (504) that includes a first electrode (506) and a second electrode (508) spaced radially apart from one another, for example in a diametrically opposed configuration. Electrodes (506, 508) are electrically coupled with a generator (512) that is operable to provide radio frequency ("RF") energy to electrodes (506, 508), for example in the frequency range of approximately 300 kilohertz (kHz) to 1 megahertz (MHz). Electrodes (506, 508) of the present example are configured to cooperate to deliver bipolar RF energy to tissue when both electrodes (506, 508) are placed in electrical contact with the tissue. In particular, one electrode (506, 508) may operate as an active electrode while the other electrode (506, 508) operates as a passive electrode. The RF energy is configured to induce ionic agitation, or friction, and in effect resistive heating, thereby increasing the temperature of the tissue in a manner sufficient for removing, shrinking, and/or sculpting tissue while simultaneously sealing blood vessels, thereby enhancing the cutting performance of cutter tube (502).

In other versions, cutter tube (502) may include a single electrode, and a grounding pad (not shown) electrically coupled with generator (512) may be placed in contact with the patient. The single electrode and the grounding pad may cooperate to deliver mono-polar RF energy to the targeted tissue to induce ionic agitation. In other versions, one or more electrodes may be provided on a portion of an auger member (not shown) of piercing instrument (500), such that the auger member is configured to treat tissue with RF energy. Moreover, it will be appreciated that the RF energy delivery features described herein in connection with FIG. 17 may be combined with the ultrasonic energy delivery features described above in connection with FIG. 16.

It will be appreciated that the energy delivery features of any of the exemplary instruments described herein may be further configured in accordance with any one or more teachings of U.S. Pat. No. 8,663,220, entitled "Ultrasonic Surgical Instruments," issued Mar. 4, 2014; U.S. Pub. No. 2017/0000541, entitled "Surgical Instrument with User Adaptable Techniques," published Jan. 5, 2017; U.S. Pat. No. 9,572,622, entitled "Bipolar Electrosurgical Features for Targeted Hemostasis," issued Feb. 21, 2017; and/or U.S. Pat. No. 9,949,785, entitled "Ultrasonic Surgical Instrument with Electrosurgical Feature," issued Apr. 24, 2018. The disclosure of each of these references is incorporated by reference herein.

D. Exemplary Auger Member with Indicia

Figure 18:
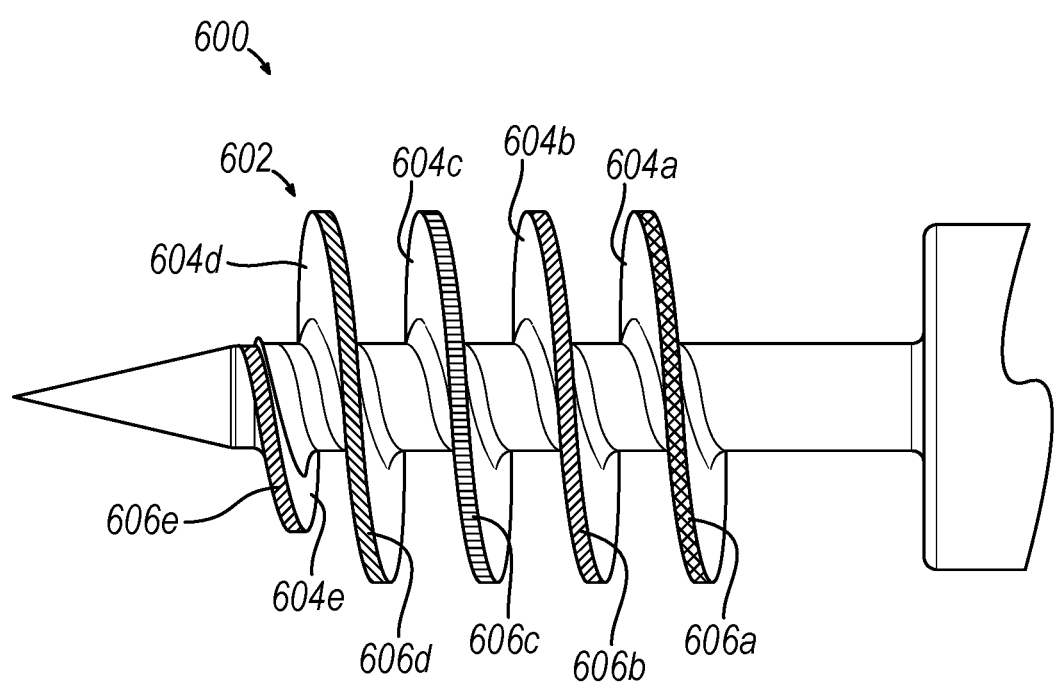
FIG. 18 depicts a schematic side elevation view of a distal cutting member of another exemplary surgical piercing instrument, showing a plurality of unique types of indicia on an outer edge of a helical blade of the cutting member.

FIG. 18 shows exemplary alternative auger member (600) having a helical blade (602) that incorporates indicia (606a, 606b, 606c, 606d, 606e) to assist a surgeon in identifying the depth to which helical blade (602) has been driven into tissue during a surgical procedure. Helical blade (602) is a continuous structure having a plurality of helical turns (604a, 604b, 604c, 604d, 604e), each wrapping at least 180 degrees (e.g., between 270 degrees and 360 degrees) about the central axis of auger member (600) and having a radially outer cutting edge. In the present version, the outer edge of first turn (604a) is provided with a first type of indicia (606a); the outer edge of second turn (604b) is provided with a second type of indicia (606b); the outer edge of third turn (604c) is provided with a third type of indicia (606c); the outer edge of fourth turn (604d) is provided with a fourth type of indicia (606d); and the outer edge of fifth turn (604e) is provided with a fifth type of indicia (606e). Indicia (606a-606e) may be in the form of color-coding, texturing, or other suitable features that are visually apparent to a surgeon, for example via an endoscope (not shown) positioned at the surgical site. Accordingly, because indicia (606a-606e) varies along the length of helical blade (602), the surgeon may quickly determine the depth to which helical blade (602) has been driven into an anatomical structure by observing the specific type of indicia (606a-606e) that remains visible outwardly of the tissue surface.

E. Exemplary Deformable Shaft Assembly

Figure 19:
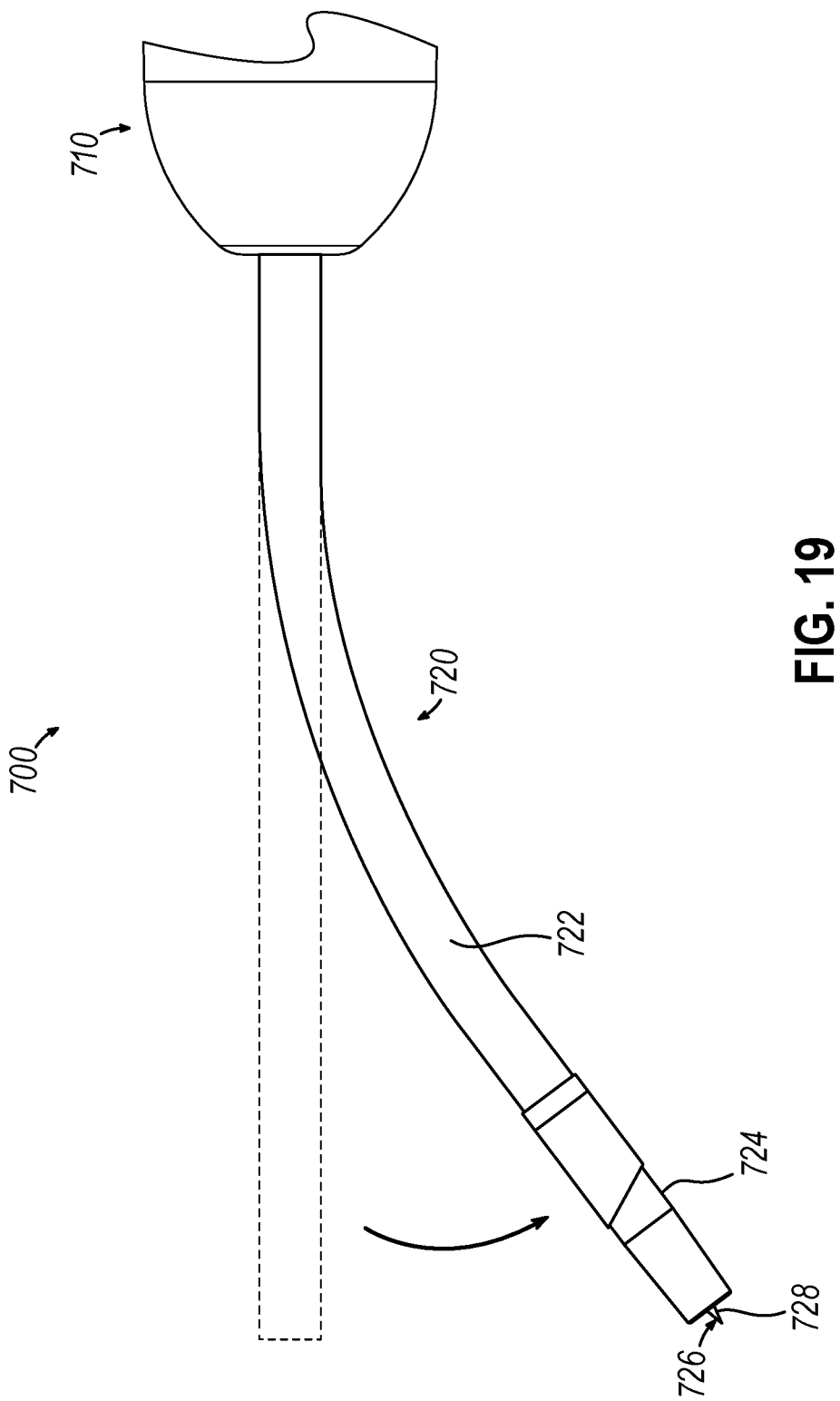
FIG. 19 depicts a schematic side elevation view of a shaft assembly of another exemplary surgical piercing instrument, showing the shaft assembly being bent by a user into a predetermined bent configuration.

FIG. 19 shows a distal portion of another exemplary surgical piercing instrument (700) that includes a handle assembly (710) and a shaft assembly (720) extending distally from handle assembly (710) along a longitudinal axis. Shaft assembly (720) includes an outer sheath (722), a cutter tube (724) slidably disposed within outer sheath (722), and a rotatable shaft (726) rotatably disposed within cutter tube (724) and having an auger member (728) at a distal end thereof. Shaft assembly (720) of the present version is configured to be plastically deformed by an operator into a bent configuration relative to the longitudinal axis before and/or after insertion into a patient. As shown in FIG. 19, and by way of example only, such a bent configuration may comprise a gradual curvature along a length of shaft assembly (720). In some versions, shaft assembly (720) may comprise a malleable material that enables the operator to bend one or more components of shaft assembly (720) manually into a desired shape before insertion into the patient. In other versions, shaft assembly (720) may include pull-wires, bands, or other steering features that extend longitudinally through shaft assembly (720) and which may be actuated by the operator to bend shaft assembly (720) into the desired shape before and/or after insertion into the patient.

Advantageously, such deformability of shaft assembly (720) may enable the operator to more easily and effectively access certain locations within the nasal cavity (NC) of a patient during a procedure, such as a particular turbinate (LT, MT, UT) or a wall of a selected paranasal sinus (FS, ES, SS). In the bent configuration, rotatable shaft (726) remains selectively rotatable relative to handle assembly (710), and cutter tube (724) and outer sheath (722) remain selectively translatable relative to handle assembly (710). Accordingly, normal function of instrument (700) is not impeded when shaft assembly (720) is in the bent configuration.

In other versions, shaft assembly (720) may be formed of suitably flexible materials such that shaft assembly (720) is configured to assume a deflected state upon application of an external force, and then resiliently return to its original straight state upon removal of the external force.

F. Exemplary Shaft Assembly Having Articulation Section

Figure 20:
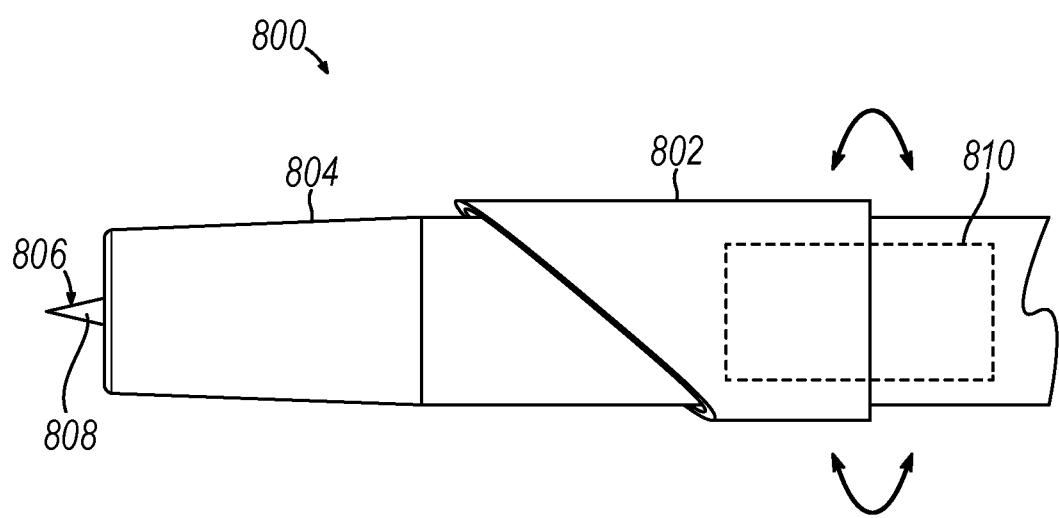
FIG. 20 depicts a schematic side elevation view of a shaft assembly of another exemplary surgical piercing instrument having an articulation section.

FIG. 20 shows a distal portion of another exemplary shaft assembly (800) configured for use with any of the exemplary surgical piercing instruments disclosed herein. Shaft assembly (800) includes an outer sheath (802), a cutter tube (804) slidably disposed within outer sheath (802), and a rotatable shaft (806) rotatably disposed within cutter tube (804) and having a distal auger member (808). Shaft assembly (800) further includes an articulation section (810) (shown schematically) configured permit lateral articulation of a distal portion of shaft assembly (800) relative a proximal portion of shaft assembly (800).

Articulation section (810) of the present version is integrated into the elongate structure of rotatable shaft (806), proximal to auger member (808). Articulation section (810) may be in the form of a flex section defined by a plurality of interlinked joints, beads, ribs, or other similar types of elements that enable shaft (806) to assume a relatively sharp bend (e.g., approximately 90 degrees) and yet still rotate while maintaining the bend. In other versions, articulation section (810) may be defined by a rotary drive cable. In further versions, articulation section (810) be defined by a flexible, narrowed section of rotatable shaft (806). In any such versions, at least a portion of cutter tube (804) and outer sheath (802) that translate over articulation section (810) during use may have a flexible construction that enables cutter tube (804) and outer sheath (802) to freely pass over articulation section (810) in an articulated state. Such flexibility may be provided via a linear arrangement of small openings, a braided structure, or various other features readily apparent to those of ordinary skill in the art.

Additionally, though not shown, in some versions shaft assembly (800) may further include one or more articulation drivers that may be selectively actuated by a user to drive articulation of shaft assembly (800) (referred to as "active articulation"). By way of example only, such articulation drivers may be in the form of one or more elongate bands or pull-wires that extend longitudinally through shaft assembly (800). The articulation drivers may be secured at their distal ends to the distal shaft portion distal to articulation section (810); and they may be secured at their proximal ends to an actuator (not shown) provided on the handle assembly from which shaft assembly (800) extends. Such an actuator may be in the form of a knob, dial, lever, or the like, for example. In other versions, such articulation drivers and actuators may be omitted, such that articulation section (810) is configured to articulate in response to the distal portion of shaft assembly (800) being pressed against a structure (referred to as "passive articulation"). Additionally, it will be appreciated that such articulation features presently described in connection with FIG. 20 may be combined with the bendability features described above in connection with FIG. 19.

G. Exemplary Additional Features for Piercing Instrument

The exemplary piercing instruments described herein may be further enhanced in various additional ways for improved performance in certain surgical procedures. For instance, and with exemplary reference to instrument (10) of FIG. 2, shaft assembly (40) may be releasably attached to handle assembly (20) such that shaft assembly (40) may be removed and replaced with a fresh shaft assembly (40) following a surgical procedure. Accordingly, handle assembly (20) may be reused for one or more subsequent surgical procedures.

In another exemplary configuration, shaft assembly (40) may include an extended internal lumen (not shown) configured to capture increased volumes of tissue extracted by auger member (60) and cutter tube (44). In another exemplary configuration, the internal lumen of shaft assembly (40) may be coupled with a suction source (not shown) configured to draw the captured tissue and fluids out of shaft assembly (40) for disposal purposes. In further exemplary configurations, though not shown, auger member (60) may be formed with geometry similar to that of a drill bit, including a proximal shank, a helical groove (or "flute"), and a pair of distal cutting edges. Various other suitable geometries for auger member (60) will be readily apparent to those of ordinary skill in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a handle assembly; (b) a shaft assembly extending distally from the handle assembly and having a distal end sized to be inserted into the nasal cavity of a patient, wherein the shaft assembly includes: (i) a cutting member configured to cut tissue within the nasal cavity, and (ii) a translating member slidably disposed over the cutting member; and (c) a navigation sensor disposed within the distal end of the shaft assembly, wherein the navigation sensor is operable to generate a signal corresponding to a position of the distal end within the patient.

Example 2

The surgical instrument of Example 1, wherein the navigation sensor includes an electromagnetic coil.

Example 3

The surgical instrument of any of the preceding Examples, wherein the navigation sensor is housed within the cutting member.

Example 4

The surgical instrument of any of the preceding Examples, wherein the shaft assembly includes a shaft and a cylindrical core extending axially within a bore of the shaft, wherein the cutting member is rigidly coupled with a distal end of the shaft, wherein the navigation sensor is housed within a distal end of the cylindrical core.

Example 5

The surgical instrument of Example 4, wherein the shaft is rotatable about the cylindrical core relative to the handle assembly, wherein the translating member is slidably disposed over the shaft and is configured to translate longitudinally relative to the handle assembly.

Example 6

The surgical instrument of Example 5, wherein the handle assembly includes a motor operable to rotate the shaft relative to the handle assembly.

Example 7

The surgical instrument of any of Examples 4 through 6, further comprising a resilient member configured to resiliently bias the cylindrical core distally within the bore of the shaft.

Example 8

The surgical instrument of any of the preceding Examples, wherein the cutting member comprises a first cutting member, wherein a distal end of the translating member defines a second cutting member configured to cut tissue within the nasal cavity.

Example 9

The surgical instrument of any of the preceding Examples, wherein the cutting member comprises a helical blade.

Example 10

The surgical instrument of Example 9, wherein the helical blade includes a plurality of turns, wherein an outer edge of each turn includes indicia.

Example 11

The surgical instrument of Example 10, wherein the outer edge of each turn includes a unique type of indicia.

Example 12

The surgical instrument of Example 10, wherein the indicia comprises a color, wherein the outer edge of each turn includes a unique color.

Example 13

The surgical instrument of any of the preceding Examples, wherein the distal end of the shaft includes an electrode operable to deliver RF energy to tissue.

Example 14

The surgical instrument of any of the preceding Examples, further comprising an ultrasonic transducer, wherein the ultrasonic transducer is configured to drive a distal portion of the shaft assembly with ultrasonic energy.

Example 15

The surgical instrument of any of the preceding Examples, wherein the shaft assembly is configured to be plastically deformed by a user into a predetermined bent configuration, wherein the shaft is configured to rotate relative to the handle assembly when the shaft assembly is in the bent configuration.

Example 16

A surgical instrument comprising: (a) a handle assembly; (b) a shaft assembly extending distally from the handle assembly and having a distal end sized to be inserted into the nasal cavity of a patient; and (c) a helical blade disposed at the distal end of the shaft assembly, wherein the helical blade is selectively rotatable relative to the handle assembly to pierce tissue within the nasal cavity, wherein the helical blade includes: (i) a first turn, wherein an outer edge of the first turn has a first type of indicia, and (ii) a second turn, wherein an outer edge of the second turn has a second type of indicia different than the first type.

Example 17

The surgical instrument of Example 16, wherein the helical blade includes at least three turns, wherein each of the three turns includes unique indicia.

Example 18

The surgical instrument of any of Examples 16 through 17, wherein the first indicia comprises a first color, wherein the second indicia comprises a second color different than the first color.

Example 19

A method of removing tissue from the nasal cavity of a patient with a surgical piercing instrument that includes a shaft assembly having a cutting member and a navigation sensor, the method comprising: (a) providing a distal end of the shaft assembly within the nasal cavity of the patient; (b) generating a signal with the navigation sensor in response to presence of the navigation sensor within an electromagnetic field generated about the head of the patient; (c) communicating the signal to a processor, wherein the processor is configured to inform a user of a location of the distal end within the nasal cavity based on the signal; and (d) cutting tissue within the nasal cavity via rotation of the cutting member.

Example 20

The surgical instrument of Example 19, further comprising rotating the cutting member about the navigation sensor while cutting the tissue.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
   (a) a handle assembly;
   (b) a shaft assembly extending distally from the handle assembly and having a distal end sized to be inserted into the nasal cavity of a patient, a portion of the shaft assembly being rotatable relative to the handle assembly, the shaft assembly including:
      (i) a cutting member configured to cut tissue within the nasal cavity, and
      (ii) a translating member slidably disposed over the cutting member; and
   (c) a navigation sensor housed within the cutting member, the navigation sensor being operable to generate a signal corresponding to a position of the distal end within the patient, the navigation sensor being rotationally fixed relative to the handle assembly, the portion of the shaft assembly that is rotatable relative to the handle assembly being further rotatable relative to the navigation sensor.

2. The surgical instrument of claim 1, the navigation sensor including an electromagnetic coil.

3. The surgical instrument of claim 1, the shaft assembly including a shaft and a cylindrical core extending axially within a bore of the shaft, the cutting member being rigidly coupled with a distal end of the shaft, the navigation sensor being housed within a distal end of the cylindrical core.

4. The surgical instrument of claim 3, the shaft being rotatable about the cylindrical core relative to the handle assembly, the translating member being slidably disposed over the shaft and is configured to translate longitudinally relative to the handle assembly.

5. The surgical instrument of claim 4, wherein the handle assembly includes including a motor operable to rotate the shaft relative to the handle assembly.

6. The surgical instrument of claim 3, further comprising a resilient member configured to resiliently bias the cylindrical core distally within the bore of the shaft, the bias being relative to the handle.

7. The surgical instrument of claim 1, the cutting member comprising a first cutting member, a distal end of the translating member defining a second cutting member configured to cut tissue within the nasal cavity.

8. The surgical instrument of claim 1, the cutting member comprising a helical blade.

9. The surgical instrument of claim 8, the helical blade including a plurality of turns, an outer edge of each turn including indicia.

10. The surgical instrument of claim 9, the outer edge of each turn including a unique type of indicia.

11. The surgical instrument of claim 9, the indicia comprising a color, the outer edge of each turn including a unique color.

12. The surgical instrument of claim 1, the distal end of the shaft including an electrode operable to deliver RF energy to tissue.

13. The surgical instrument of claim 1, further comprising an ultrasonic transducer, the ultrasonic transducer being configured to drive a distal portion of the shaft assembly with ultrasonic energy.

14. The surgical instrument of claim 1, the shaft assembly being configured to be plastically deformed by a user into a predetermined bent configuration, the shaft being configured to rotate relative to the handle assembly when the shaft assembly is in the bent configuration.

\* \* \* \* \*